(12) United States Patent
Houjou

(10) Patent No.: US 8,956,861 B2
(45) Date of Patent: Feb. 17, 2015

(54) CONTAINER TRAY, TRAY BASE, AND OBSERVATION UNIT

(75) Inventor: Mikio Houjou, Higashiosaka (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 328 days.

(21) Appl. No.: 13/617,036

(22) Filed: Sep. 14, 2012

(65) Prior Publication Data

US 2013/0008266 A1 Jan. 10, 2013

Related U.S. Application Data

(63) Continuation-in-part of application No. PCT/JP2011/056089, filed on Mar. 15, 2011.

(30) Foreign Application Priority Data

Mar. 17, 2010 (JP) .................................. 2010-060454

(51) Int. Cl.
*G02B 21/34* (2006.01)
*B01L 9/00* (2006.01)
(Continued)

(52) U.S. Cl.
CPC ........ *G02B 21/34* (2013.01); *G01N 2021/0375* (2013.01); *G02B 21/26* (2013.01); *B01L 9/52* (2013.01); *C12M 23/10* (2013.01); *C12M 41/36* (2013.01)
USPC .................. 435/305.1; 73/864.91; 211/126.1; 312/126; 312/209; 359/391; 422/561; 435/288.3; 435/288.7; 435/305.4

(58) Field of Classification Search
CPC ......... B01L 9/52; C12M 23/04; C12M 23/10; C12M 41/36; G01N 2021/0375; G02B 21/26; G02B 21/34

USPC ............ 73/864.91; 211/126.1; 312/126, 209; 356/244; 359/391; 422/555, 561; 435/288.3, 288.7, 305.1, 305.4

See application file for complete search history.

(56) References Cited

U.S. PATENT DOCUMENTS 3,547,505 A * 12/1970 Ott et al. .................... 312/209 X
5,782,448 A * 7/1998 Withun et al. ............. 248/311.2
(Continued)

FOREIGN PATENT DOCUMENTS

JP            10053059 A * 2/1998 ............... B60N 3/00
JP      2006-171227 A      6/2006
(Continued)

OTHER PUBLICATIONS

Google machine translation of WO 2011/115127 A1, WO 2011/115127 A1 was published Sep. 22, 2011.*

(Continued)

*Primary Examiner* — Thomas P Noland
(74) *Attorney, Agent, or Firm* — Westerman, Hattori, Daniels & Adrian, LLP

(57) ABSTRACT

Provided are a container tray in which a position and orientation of a container is hardly displaced from a predetermined position and orientation; a tray base used together with the container tray; and an observation unit. The container tray 8 includes a mounting plate 81 having a mounting surface 811 on which the container is to be mounted, an elastic body 82, and a biasing mechanism 83, 842. The elastic body 82 is arranged on the mounting surface 811 of the mounting plate 81 around a mounting region R where the container is to be mounted. The biasing mechanism 83, 842 is capable of switching states between a biased state in which the elastic body 82 is biased inward by applying a pressing force to the elastic body 82 from outside and a bias released state in which the bias on the elastic body 82 is released.

12 Claims, 12 Drawing Sheets

(51) Int. Cl.
*C12M 1/00* (2006.01)
*C12M 1/34* (2006.01)
*G01N 21/01* (2006.01)
*G02B 21/26* (2006.01)
*C12M 1/22* (2006.01)
*G01N 21/03* (2006.01)

(56) References Cited

U.S. PATENT DOCUMENTS

2004/0237670 A1* 12/2004 Koo et al. ............. 73/864.91 X
2005/0007581 A1* 1/2005 Harris et al. ................. 356/244
2006/0128005 A1 6/2006 Hasegawa et al.
2007/0065936 A1 3/2007 Hasegawa et al.
2009/0175763 A1* 7/2009 Malin .............................. 422/65
2013/0183751 A1* 7/2013 Kobayashi et al. ........ 435/287.3
2014/0182020 A1* 6/2014 Suh ................................ 850/18

FOREIGN PATENT DOCUMENTS

JP 2006-189470 A 7/2006
JP 2007-111034 A 5/2007
JP 2007-330143 A 12/2007
JP 2011038923 A * 2/2011 ............... C12M 1/34

OTHER PUBLICATIONS

International Preliminary Report on Patentability PCT/JP2011/056089, report issued Oct. 23, 2012.*
International Search Report of PCT/JP2011/056089, mailing date Jun. 7, 2011, 2 pages.

* cited by examiner

F I G. 3
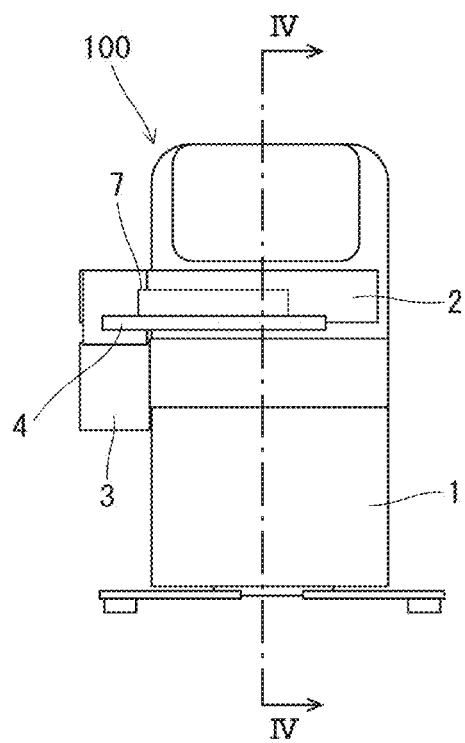
F I G. 4
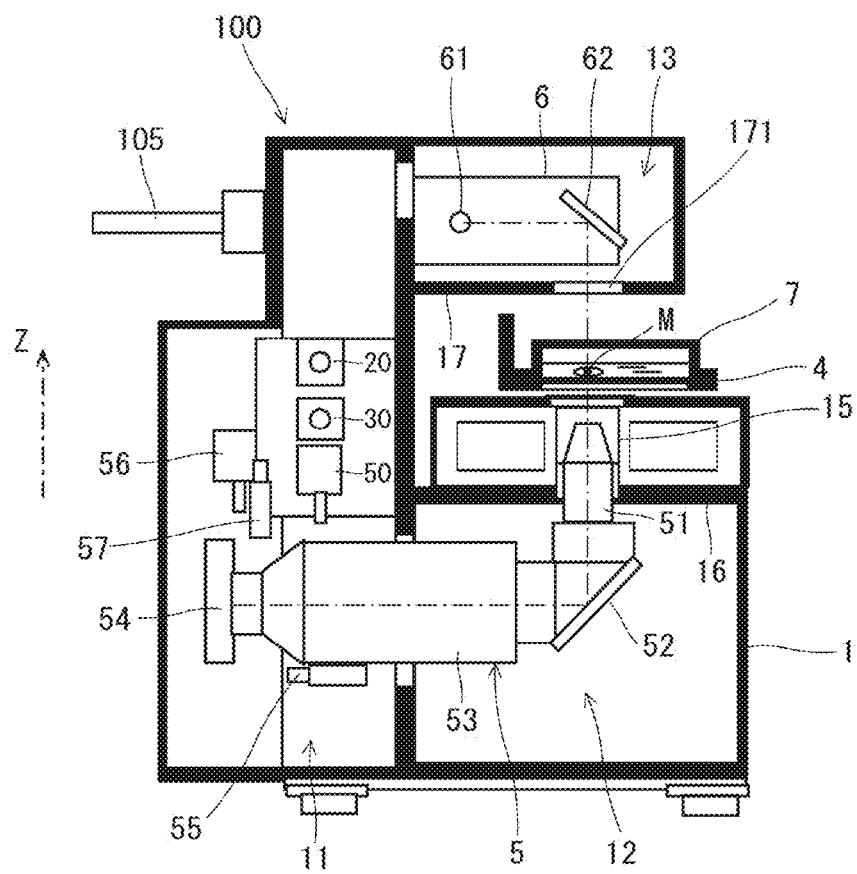

F I G. 9
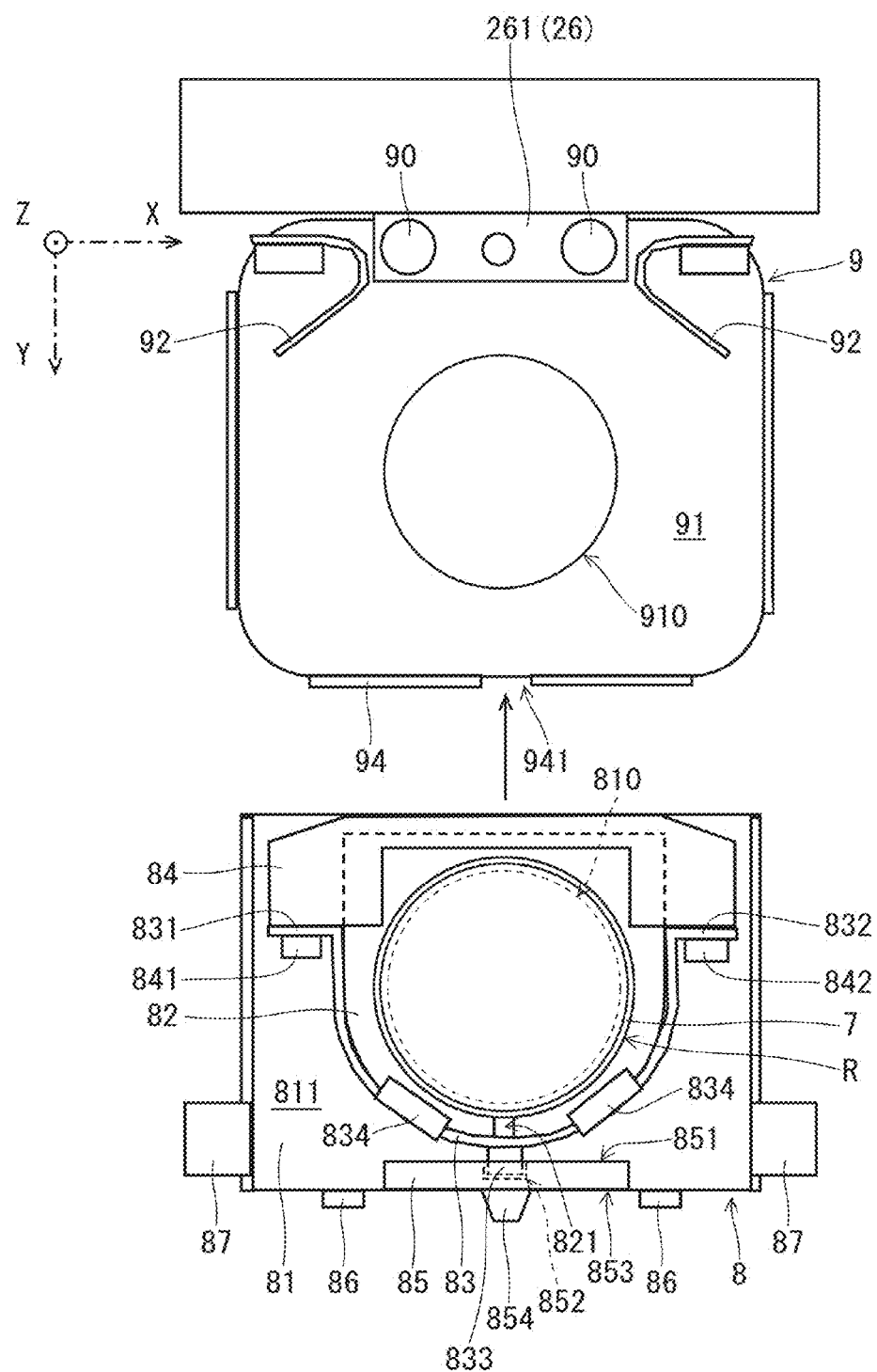

CONTAINER TRAY, TRAY BASE, AND OBSERVATION UNIT

CROSS-REFERENCE TO RELATED APPLICATIONS

This application is a continuation-in-part application of Patent Cooperation Treaty Patent Application Number PCT/JP2011/056089 (filed on Mar. 15, 2011), which claims priority from Japanese patent application JP2010-060454 (filed on Mar. 17, 2010), all of which are hereby incorporated by reference herein in their entirety.

TECHNICAL FIELD

The present invention relates to a container tray used in an observation unit for observing a sample such as a cell, a tray base used together with the container tray, and the observation unit.

BACKGROUND ART

This type of observation unit is used in a storage such as an incubator, and includes a mounting table on which a container containing a sample such as a cell together with a culture medium is to be mounted, a driving mechanism that moves the mounting table along a horizontal plane, and an observation device that observes the sample in the container to acquire an observed image of the sample. The observation device can vertically move with respect to the mounting table. In this observation unit, the mounting table is moved along the horizontal plane, and the observation device is vertically moved to adjust a focus, so that the sample in the container is observed.

Further, in the observation unit, coordinates and the focus position of the sample are recorded as sample information in a memory. One or more samples can be observed based on the sample information on a certain cycle by using the observation device, and a time lapse operation of acquiring the observed image of the sample can be performed at each observation.

When a predetermined period elapses from the start of the time lapse operation, the culture medium in the container is soiled with growth of the sample, and nutrition contained in the culture medium decreases. Accordingly, the culture medium in the container needs to be exchanged or resupplied. When this exchange or resupply operation (hereinafter referred to as "exchange operation") is performed, the container is moved from the mounting table to another place. After completion of the exchange operation, the container is mounted on the mounting table again. At this time, it is difficult to mount the container at the same position and orientation as the position and orientation before the exchange operation of the culture medium on the mounting table. For this reason, the position and orientation of the container vary before and after the exchange operation of the culture medium. Accordingly, the sample information recorded in the memory becomes invalid, and the sample information must be set again in order to continue the time lapse operation.

In contrast, a window may be provided in the storage, and by putting a hand from the window, the exchange operation of the culture medium may be performed without moving the container on the mounting table. However, an operational range via the window is narrow and thus, it is difficult to perform the exchange operation of the culture medium without moving the container. Alternatively, the container may be provided with a marker, and when the position and orientation of the container is displaced before and after the exchange operation of the culture medium, coordinates and the focus position of the sample, which correspond to the coordinates and the focus position recorded in the memory, may be calculated based on the position of the marker. The available container will be limited to a specific container having the marker, thereby type of the container is limited.

Thus, an observation unit including a tray base attached to the driving mechanism, and a container tray detachably attached to the tray base has been proposed (refer to, for example, Patent Document 1). Specifically, the container tray is positioned at a predetermined position with respect to the tray base by a pin. The container tray has an insertion hole for inserting the container thereinto, and an inner surface of the insertion hole has a plurality of protrusions. Accordingly, when the container is inserted into the insertion hole, each of the protrusions is elastically deformed, so that a biasing force (elastic force) is applied from each of the protrusions toward the container. As a result, the container is held by the plurality of protrusions to fix the container to the container tray.

As another technique of fixing the container to the container tray, a technique of fixing the container by using a slide pin is proposed (refer to, for example, Patent Document 2). Specifically, the container tray has an insertion hole for inserting the container thereinto, an inner surface of the insertion hole has a horizontal hole, and the slide pin is slidably stored in the horizontal hole. The slide pin is biased toward the inner side of the insertion hole by a spring, and a front end of the slide pin protrudes from an inner surface of a hole for the container. A knob for a sliding operation is attached to the slide pin. A plurality of fixing pins are provided on the inner surface of the insertion hole.

PRIOR ART DOCUMENTS

Patent Documents

Patent Document 1: Japanese Patent Laid-open Publication No. 2007-330143

Patent Document 2: Japanese Patent Laid-open Publication No. 2006-189470

SUMMARY OF THE INVENTION

Problems to be Solved by the Invention

In the observation unit (Patent Document 1), when the exchange operation of the culture medium in the container is performed, the container tray is detached from the tray base in a condition where the container is fixed to the container tray. Then, after the completion of the exchange operation, the container tray is reattached to the tray base. At this time, the container tray is positioned at the predetermined position on the tray base by the pin. The container remains to be fixed to the container tray. Accordingly, in the observation unit, as compared to the above-mentioned conventional observation unit, the position and orientation of the container are hardly displaced before and after the exchange operation.

However, when the container is inserted into the insertion hole in the observation unit, the container is pressed with its side surface being subjected to the biasing force from the protrusions. For this reason, a frictional force is generated between the side surface of the container and the protrusions, and the protrusions are elastically deformed in an inserting direction of the container by the frictional force. Accordingly, a force to push the container out of the insertion hole is applied from the protrusions to the container. As a result, the container may float from the predetermined position on the container tray, or a container holding force of the protrusions may be reduced to rotate the container in the insertion hole. When the position and/or orientation of the container is displaced from the predetermined position and/or orientation, similarly to the conventional observation unit, the sample information recorded in the memory may become invalid, and the sample information may be required to be set again to continue the time lapse operation.

According to another technique described above (Patent Document 2), when the container is inserted into the insertion hole, first, the user operates the knob to slide the slide pin against the biasing force of the spring, so that the front end of the slide pin is embedded in the horizontal hole. Thus, when the container is inserted, the container is not subjected to the biasing force of the slide pin. When the user releases the knob, the slide pin slides due to the biasing force of the spring, and consequently, the front end of the slide pin is brought into contact with the side surface of the container. In this manner, the container is held by the slide pin and the fixing pin due to the biasing force of the spring, and the container is fixed to the container tray.

However, according to this technique, the slide pin is slidably received in the horizontal hole. Accordingly, a wobble easily occurs in the slide pin. Even when the container is fixed to the container tray, the position and/or orientation of the container may be displaced from the predetermined position and/or orientation by the wobble of the slide pin. When the position and/or orientation of the container is displaced from the predetermined position and/or orientation, similarly to the conventional observation unit, the sample information recorded in the memory may become invalid, and the sample information may be required to be set again to continue the time lapse operation.

There exist a flask-shaped container with a cap and a circular dish-shaped container having a cover. Various materials such as plastic and glass may be used as the material for the container. The circular dish-shaped container is suitable for cultivation of the sample since it has a large opening and the sample in the container is easy to handle (for example, a peeling operation is easy). However, when the container is circular, according to the above-mentioned conventional technique, it is considered difficult to restrict the rotation of the container. When the side surface of the container is inclined, according to the above-mentioned technique, the force pushing the container out of the insertion hole is easily applied from the protrusions and the slide pin.

Therefore, an object of the present invention is to provide a container tray in which the position and orientation of the container are hardly displaced from the predetermined position and orientation, a tray base used together with the container tray, and an observation unit.

Means for Solving the Problems

A container tray according to the present invention includes a mounting plate having a mounting surface on which a container is to be mounted, an elastic body, and a biasing mechanism. The elastic body is arranged on the mounting surface of the mounting plate around a mounting region where the container is to be mounted. The biasing mechanism is arranged around the elastic body, and is capable of switching states between a biased state in which the elastic body is biased inward by applying a pressing force to the elastic body from outside and a bias-released state in which the bias on the elastic body is released. When the biasing mechanism is set to the bias-released state, there is a small gap between the elastic body and the mounting region of the container.

In the container tray, when the container is mounted on the mounting surface of the mounting plate, the biasing mechanism is set to the bias released state. At this time, there is the small gap between the elastic body and the mounting region of the container. For this reason, when the container is mounted on the mounting region, the side surface of the container is hardly brought into contact with the elastic body, and thus, the elastic body is prevented from being elastically deformed downward due to a frictional force generated between the side surface of the container and the elastic body. Accordingly, the container does not receive the biasing force that causes the container to float from the mounting surface from the elastic body, and the container is mounted to and closely adhered on the mounting surface.

Next, the biasing mechanism is set to the biased state. At this time, the elastic body is biased inward by applying the pressing force to the elastic body from the outside. For this reason, the elastic body is pressed on the side surface of the container and closely adhered to the side surface, and consequently, the container is held by the elastic body. Accordingly, the container is fixed in the mounting region of the mounting surface by the elastic body. While the elastic body is pressed onto the side surface of the container by the biasing mechanism, a wobble hardly occurs.

Thus, in the container tray, the container is fixed on the mounting surface of the mounting plate, and is maintained in a condition where the container is closely adhered on the mounting surface. Accordingly, the position and orientation of the container are hardly displaced from the predetermined position and orientation determined when the container is fixed to the container tray.

In a specific configuration of the container tray, the biasing mechanism is provided with a blocking member that blocks the elastic body from moving in a direction perpendicular to the mounting surface.

In the container tray, when the biasing mechanism is set to the biased state and the elastic body is pressed onto the side surface of the container, the elastic body may be subjected to the force that causes the elastic body to float from the mounting surface. However, according to the specific configuration, the floating of the elastic body is prevented by the blocking member. Thus, the container is maintained in a condition where the container is closely adhered on the mounting surface.

In another specific configuration of the container tray, the elastic body extends along an outer edge of the mounting region of the container in a C-shaped, or is formed of a plurality of elastic body pieces arranged around the mounting region of the container.

A tray base according to the present invention includes an arrangement surface on which the container tray is arranged and a positioning part that detachably fixes the container tray at a predetermined position on the arrangement surface.

In the tray base, when the exchange operation of the culture medium in the container is performed, the container tray can be detached from the tray base with the container fixed to the container tray. Then, after the completion of the exchange operation, the container tray can be reattached to the tray base. Even if the container tray is detached from the tray base in this manner, when the container tray is reattached to the tray base, the container tray is positioned at the predetermined position on the arrangement surface by the positioning part of the tray base.

An observation unit according to the present invention includes a mounting table on which the container is to be mounted, a driving mechanism that drives the mounting table, and an observation device that observes a sample in the container mounted on the mounting table. The mounting table is formed of the container tray and a tray base on which the container tray is arranged, and the container tray and the tray base are each provided with a positioning mechanism that detachably fixes the container tray to the tray base at a predetermined position.

In the observation unit, when the exchange operation of the culture medium in the container mounted on the mounting table is performed, the container tray can be detached from the tray base with the container fixed to the container tray. Then, after the completion of the exchange operation, the container tray can be reattached to the tray base. Even if the container tray is detached from the tray base in this manner, when the container tray is reattached to the tray base, the container tray is positioned at the predetermined position on the tray base by the positioning mechanism. The position and orientation of the container are not displaced from the predetermined position and orientation while the container remains fixed to the container tray. Accordingly, in the observation unit, the position and orientation of the container are hardly displaced before and after the exchange operation of the culture medium.

Effects of the Invention

In a container tray, a tray base, and an observation unit according to the present invention, a position and orientation of a container are hardly displaced from a predetermined position and orientation.

BRIEF DESCRIPTION OF THE DRAWINGS

FIG. 3 is a front view showing the observation unit.

FIG. 4 is a sectional view taken along line IV-IV shown in FIG. 3.

FIG. 9 is a top view showing a state where the container tray is detached from the tray base in the mounting table.

EMBODIMENT FOR CARRYING OUT THE INVENTION

An embodiment of the present invention will be specifically described below with reference to the drawings.

1. Observation System

Figure 1:
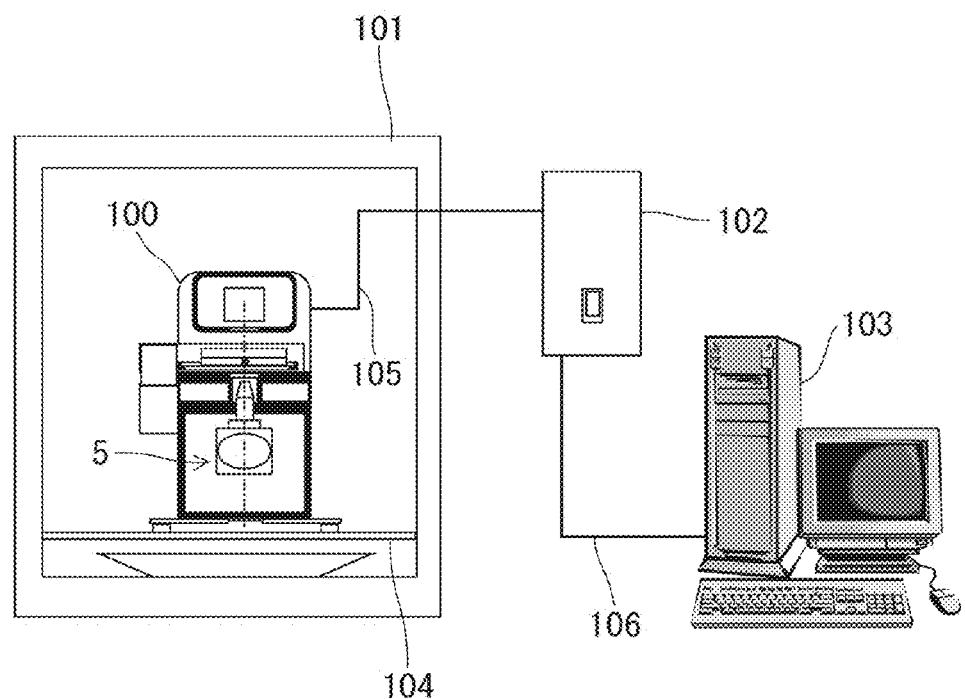
FIG. 1 is a view showing an observation system including an observation unit according to an embodiment of the present invention.

FIG. 1 is a view showing an observation system including an observation unit according to one embodiment of the present invention. As shown in FIG. 1, the observation system includes an observation unit 100, a relay control part 102, and a personal computer 103.

The observation unit 100 can be arranged in a storage 101 that cultivates or stores a sample such as a cell. An incubator capable of setting an environment in the storage 101 to be suitable for the cultivation of the sample, or an isolator capable of keeping the environment in the storage 101 biologically clean can be adopted for the storage 101. Details of the observation unit 100 will be described later in "2. Observation unit".

A shelf 104 is arranged inside the storage 101, and the observation unit 100 is used by being placed on the shelf 104. Although only one shelf 104 is provided in the storage 101 in FIG. 1, a plurality of shelves may be arranged in the storage 101. In the storage 101, a plurality of containers can be placed on the plurality of shelves, a sample can be contained in each of the containers, and the sample can be cultivated or stored. In the observation system of this embodiment, a sample attached to a bottom surface of the container, such as an attached cell, is contained in the container.

The relay control part 102 and the personal computer 103 are arranged outside the storage 101, and a cable 105 drawn from the observation unit 100 is connected to the relay control part 102. A cable 106 drawn from the relay control part 102 is connected to the personal computer 103. Details of the relay control part 102 and the personal computer 103 will be described later in "3. Relay control part" and "4. Personal computer".

2. Observation Unit 2-1. Overall Configuration of Observation Unit

Figure 2:
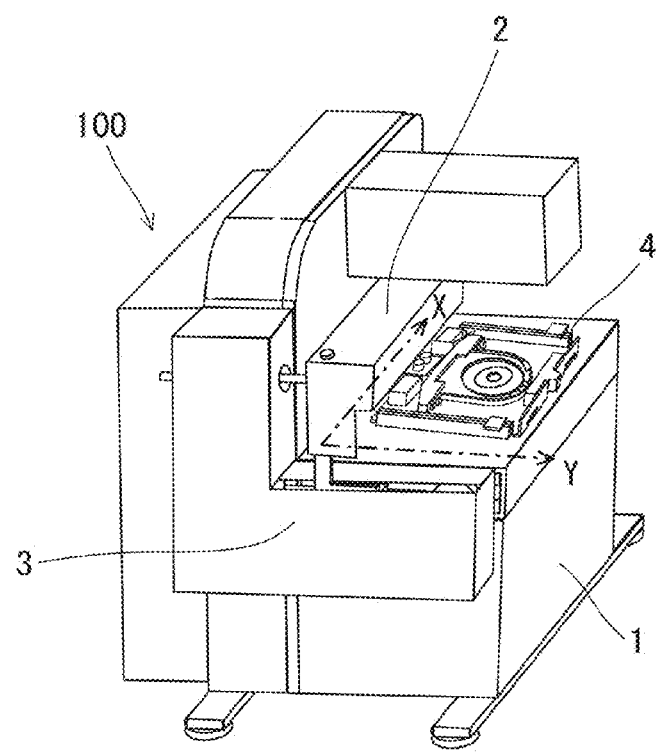
FIG. 2 is a perspective view showing the observation unit.

FIG. 2 is a perspective view showing the observation unit 100. FIG. 3 is a front view showing the observation unit 100. FIG. 4 is a sectional view taken along line IV-IV in FIG. 3. As shown in FIG. 2 to FIG. 4, the observation unit 100 includes a mounting table 4 on which a container 7 containing a sample therein is to be mounted, an X-axis driving part 2 that drives the mounting table 4 along an X-axis direction, a Y-axis driving part 3 that drives the mounting table 4 along a Y-axis direction, an observation device 5 that observes the sample in the container 7 and acquires an observed image of the sample, an illuminating device 6 that illuminates the sample when observing the sample with use of the observation device 5, a Z-axis motor 56 that moves the observation device 5 along a Z-axis direction, and a housing 1 that arranges these components therein. The X-axis direction and the Y-axis direction are two directions orthogonal to each other on the horizontal plane, and the Z-axis direction is a vertical direction.

Figure 5A:
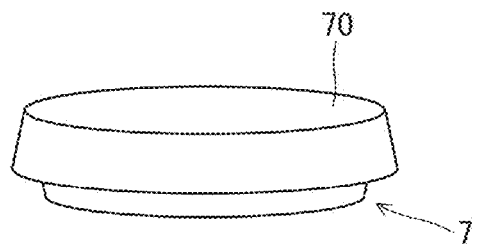
FIG. 5A is a perspective view showing a container.
Figure 5B:
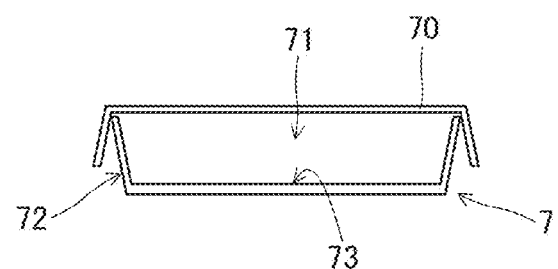
FIG. 5B is a vertical sectional view showing the container.

In the observation unit 100 of this embodiment, the X-axis driving part 2 and the Y-axis driving part 3 configure the driving mechanism that drives the mounting table 4. The container 7 has a circular dish-shaped as shown in FIG. 5A, and has a cover 70 that covers an opening 71 of the container 7 (refer to FIG. 5B). As shown in FIG. 5B, a side surface 72 of the container 7 is inclined such that the opening 71 of the container 7 is larger than a bottom surface 73.

As shown in FIG. 4, an internal space of the housing 1 is formed of a first space 11 that is horizontally displaced from the mounting table 4 and extends in a substantially vertical direction, a second space 12 located below the mounting table 4, and a third space 13 located above the mounting table 4.

2-2. X-Axis Driving Part and Y-Axis Driving Part

Figure 6:
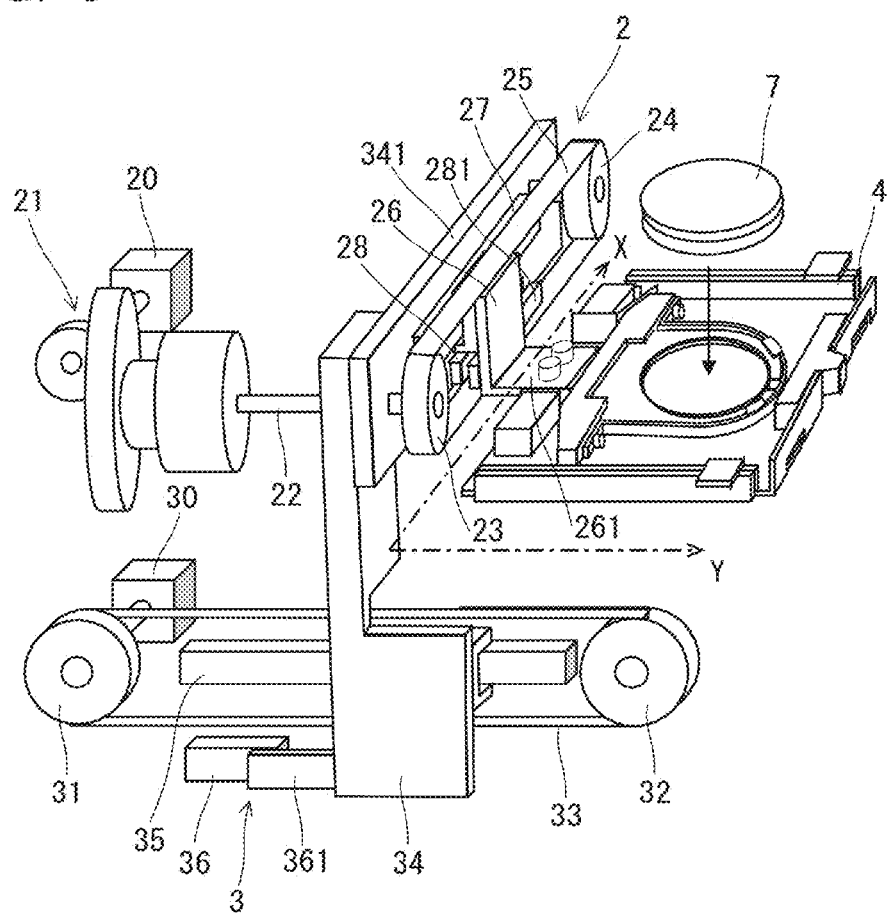
FIG. 6 is a perspective view showing an X-axis driving part and a Y-axis driving part included in the observation unit.

FIG. 6 is a perspective view showing the X-axis driving part 2 and the Y-axis driving part 3. Of the two driving parts 2, 3, first, a configuration of the Y-axis driving part 3 will be described. As shown in FIG. 6, the Y-axis driving part 3 includes a Y-axis motor 30, a pair of pulleys 31, 32, a timing belt 33, an inverted L-shaped Y-axis sliding body 34, and a guide member 35. The Y-axis motor 30 of the Y-axis driving part 3 is arranged in the first space 11 of the housing 1 as shown in FIG. 4, and its rotational shaft is oriented along the X-axis direction. A stepping motor is used as the Y-axis motor 30.

One pulley 31 of the pair of pulleys 31, 32 is fixed to the rotational shaft of the Y-axis motor 30, and the pulley 31 rotates around a rotational center axis of the Y-axis motor 30 with the rotation of the Y-axis motor 30. The other pulley 32 is rotatably arranged at a position displaced from the pulley 31 in the Y-axis direction.

A timing belt 33 extends between the pair of pulleys 31, 32, and the Y-axis sliding body 34 is coupled to a region of the timing belt 33 between the pair of pulleys 31, 32. An upper side 341 of the Y-axis sliding body 34 extends in the space where the mounting table 4 is arranged in the X-axis direction.

The guide member 35 extends between the pair of pulleys 31, 32 along the Y-axis direction, and the Y-axis sliding body 34 is slidably coupled to the guide member 35. Accordingly, the direction in which the Y-axis sliding body 34 can be moved is defined along the Y-axis direction.

In the Y-axis driving part 3, the timing belt 33 rotates together with the rotation of the one pulley 31, and the timing belt 33 moves between the pair of pulleys 31, 32 along the Y-axis direction. That is, the rotational motion of the one pulley 31 is converted into a translational motion in the Y-axis direction by the timing belt 33. Thus, in the Y-axis driving part 3, a rotational force of the Y-axis motor 30 is converted into a translational force in the Y-axis direction, and the translational force is applied to the Y-axis sliding body 34. As a result, the Y-axis sliding body 34 moves along the Y-axis direction.

As shown in FIG. 6, the X-axis driving part 2 includes an X-axis motor 20, a gear mechanism 21, a shaft 22 extending in the Y-axis direction, a pair of pulleys 23, 24, a timing belt 25, an L-shaped X-axis sliding body 26, and a guide member 27. The X-axis motor 20 of the X-axis driving part 2 is arranged in the first space 11 of the housing 1 as shown in FIG. 4, and its rotational shaft is oriented along the X-axis. A stepping motor is used as the X-axis motor 20.

The gear mechanism 21 converts a rotational force of the X-axis motor 20 into a rotational force around the center axis of the shaft 22, and the rotational force is applied to the shaft 22. The shaft 22 is rotatably supported by the upper side 341 of the Y-axis sliding body 34 of the Y-axis driving part 3, and can slide with respect to the gear mechanism 21.

One pulley 23 of the pair of pulleys 23, 24 is fixed to a front end of the shaft 22, and the pulley 23 rotates around the same center axis as that of the shaft 22 with the rotation of the shaft 22. The other pulley 24 is rotatably arranged on the upper side 341 of the Y-axis sliding body 34 at a position displaced from the pulley 23 in the X-axis direction.

The timing belt 25 extends between the pair of pulleys 23, 24, and the X-axis sliding body 26 is coupled to a region of the timing belt 25 between the pair of pulleys 23, 24. The mounting table 4 is fixed to a lower side 261 of the X-axis sliding body 26 by screws.

The guide member 27 extends between the pair of pulleys 23, 24 in the X-axis direction, and the X-axis sliding body 26 is slidably coupled to the guide member 27. Accordingly, a direction in which the X-axis sliding body 26 can be moved is defined along the X-axis direction.

In the X-axis driving part 2, the timing belt 25 rotates together with the rotation of the pulley 23, and the timing belt 25 moves between the pair of pulleys 23, 24 along the X-axis direction. That is, a rotational motion of the pulley 23 is converted into a translational motion along the X-axis direction by the timing belt 25. Thus, in the X-axis driving part 2, a rotational force of the X-axis motor 20 is converted into a translational force in the X-axis direction and the translational force is applied to the X-axis sliding body 26. As a result, the X-axis sliding body 26 moves in the X-axis direction.

Thus, the mounting table 4 fixed to the X-axis sliding body 26 moves along the X-axis direction with the rotation of the X-axis motor 20, and the mounting table 4 moves along the Y-axis direction with the rotation of the Y-axis motor 30. Accordingly, by independently controlling the rotating operation of the X-axis motor 20 and the rotating operation of the Y-axis motor 30, the mounting table 4 can be moved to various positions in the XY coordinate system.

As shown in FIG. 6, the X-axis driving part 2 further includes an X-axis origin sensor 28, and the Y-axis driving part 3 further includes a Y-axis origin sensor 36. The X-axis origin sensor 28 is a sensor that is turned ON/OFF according to approaching/separation of a detected plate 281 fixed to the X-axis sliding body 26. The Y-axis origin sensor 36 is a sensor that is turned ON/OFF according to approaching/separation of a detected plate 361 fixed to the Y-axis sliding body 34.

When the X-axis origin sensor 28 is turned ON, the position of the mounting table 4 corresponds with X-axis origin, and when the Y-axis origin sensor 36 is turned ON, the position of the mounting table 4 corresponds with a Y-axis origin. Accordingly, the X-axis origin sensor 28 and the Y-axis origin sensor 36 can return the mounting table 4 to the origin from any position displaced from the origin in the XY coordinate system in a movable range.

2-3. Illuminating Device

As shown in FIG. 4, the illuminating device 6 is arranged in the third space 13 of the housing 1, and includes an LED (Light Emitting Diode) 61 that emits light and a reflecting mirror 62 that reflects the light emitted from the LED 61 downward in the vertical direction.

A lower wall 17 forming the third space 13 of the housing 1 has a transmissive part 171 below the reflecting mirror 62. Accordingly, the light reflected by the reflecting mirror 62 passes through the transmissive part 171 and then, passes downward in a space where the mounting table 4 is arranged.

In the space where the mounting table 4 is arranged, an observation point M of the sample is set at a position where the light reflected by the reflecting mirror 62 passes. Accordingly, in the observation unit 100, the sample arranged at the observation point M can be illuminated by the illuminating device 6.

2-4. Observation Device

In this embodiment, a phase microscope is adopted as the observation device 5. As shown in FIG. 4, the observation device 5 includes an objective lens 51 that forms an enlarged image of the sample as an observed target, a reflecting mirror 52 that guides the enlarged image formed by the objective lens 51 to a zoom lens 53, the zoom lens 53 that further enlarges the enlarged image of the sample, a CCD (Charge Coupled Device) camera 54 that takes the enlarged image enlarged by the zoom lens 53 to acquire the observed image of the sample, and a driving motor 50 that drives the zoom lens 53 to change a magnification factor of the zoom lens 53.

In the observation device 5, the CCD camera 54 and the driving motor 50 are arranged in the first space 11 of the housing 1, and the objective lens 51 and the reflecting mirror 52 are arranged in the second space 12 of the housing 1. The zoom lens 53 is arranged across the first space 11 and the second space 12. The objective lens 51 is arranged below the observation point M.

An upper wall 16 forming the second space 12 of the housing 1 has a transmissive part 15 below the observation point M, and the light reflected by the reflecting mirror 62 of the illuminating device 6 passes through the observation point M, and then passes the transmissive part 15 to be incident on the objective lens 51 of the observation device 5. Therefore, in the observation unit 100, the observation device 5 can observe the sample to acquire the observed image of the sample while illuminating the sample with the illuminating device 6.

As shown in FIG. 4, an observation factor of the observation device 5 for the sample is determined depending on a magnification factor of the objective lens 51 and the magnification factor of the zoom lens 53, and the observation factor for the sample is changed by driving the zoom lens 53 with the driving motor 50 and changing the magnification factor of the zoom lens 53.

Focusing during observation of the sample with the observation device 5 is performed by moving the observation device 5 along the Z-axis direction with the Z-axis motor 56. As shown in FIG. 4, the Z-axis motor 56 is arranged in the first space 11 of the housing 1.

As shown in FIG. 4, the observation device 5 further includes a zoom original sensor 55. The zoom original sensor 55 is a sensor that is turned ON/OFF according to approaching/separation of a detected plate (not shown) fixed to the zoom lens 53. When the zoom original sensor 55 is turned ON, the position of the zoom lens 53 corresponds with a predetermined position. The zoom original sensor 55 can return the zoom lens 53 to the predetermined position from any position displaced from the predetermined position in a movable range.

Further, a Z-axis origin sensor 57 is arranged in the first space 11 of the housing 1. The Z-axis origin sensor 57 is a sensor that is turned ON/OFF according to approaching/separation of a detected plate (not shown) fixed to the observation device 5. When the Z-axis origin sensor 57 is turned ON, the position of the observation device 5 corresponds with a Z-axis origin. The Z-axis origin sensor 57 can return the observation device 5 to the origin from any position displaced from the origin in the Z-axis direction in a movable range.

2-5. Mounting Table

<Overall Configuration of Mounting Table>

Figure 7:
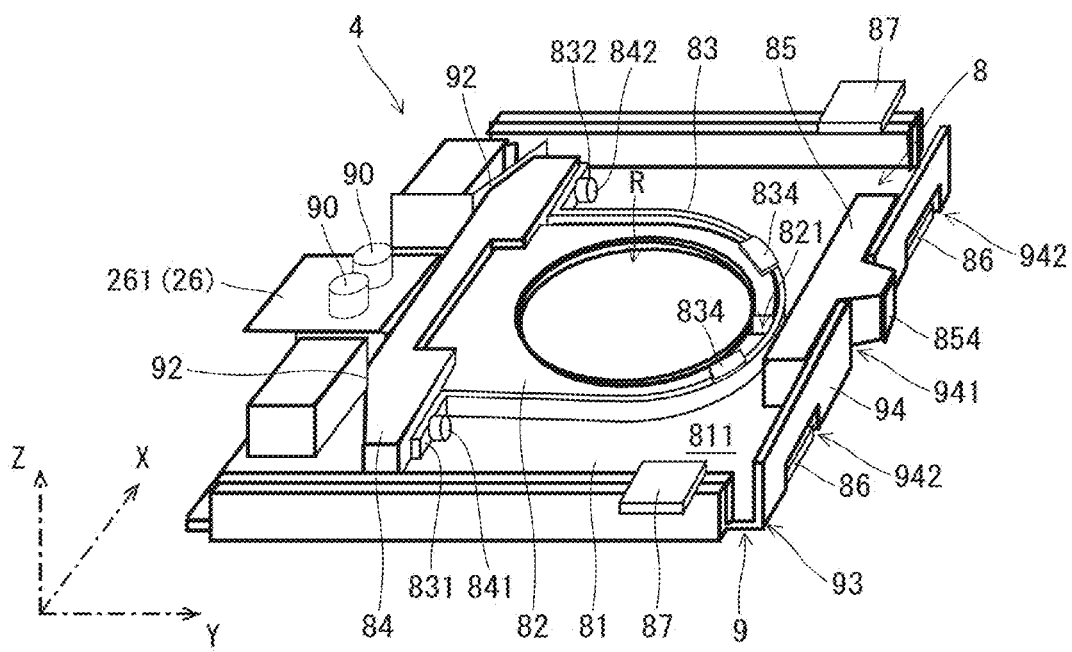
FIG. 7 is a perspective view showing a mounting table included in the observation unit.
Figure 8:
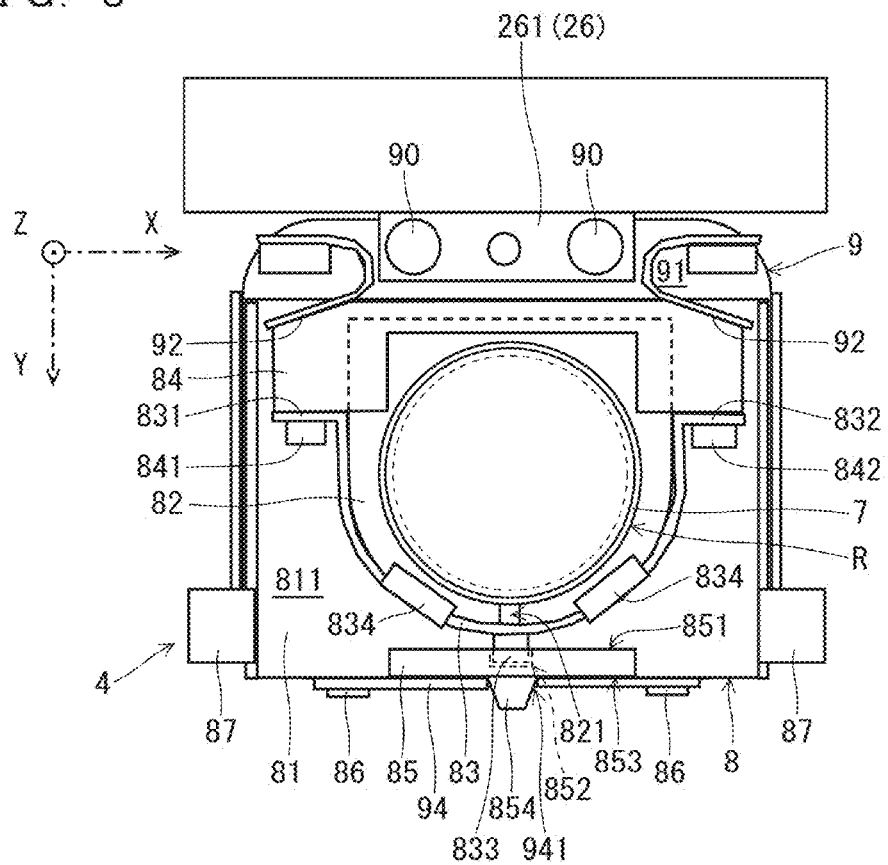
FIG. 8 is a top view showing a state where a container tray is arranged on a tray base in the mounting table.

FIG. 7 is a perspective view showing the mounting table 4. FIG. 8 and FIG. 9 are top views showing the mounting table 4. In FIG. 8 and FIG. 9, the cover 70 of the container 7 is not shown. As shown in FIG. 7 to FIG. 9, the mounting table 4 is formed of a container tray 8 that fixes the container 7 and a tray base 9 on which the container tray 8 is arranged. FIG. 7 and FIG. 8 show a state where the container tray 8 is arranged on the tray base 9, and FIG. 9 shows a state where the container tray 8 is detached from the tray base 9.

As shown in FIG. 9, the container tray 8 includes amounting plate 81 having a mounting surface 811 on which the container 7 is to be mounted. The mounting plate 81 has a through hole 810 on the inner side of amounting region R of the container 7. The mounting region R of the container 7 is a region that overlaps the bottom of the container 7 when the container 7 is placed on the mounting surface 811. The tray base 9 has a through hole 910 that is opposed to the through hole 810 of the container tray 8 when the container tray 8 is arranged on the tray base 9.

Accordingly, as shown in FIG. 4, light reflected by the reflecting mirror 62 of the illuminating device 6 passes through the two through holes 810, 910 to be incident on the objective lens 51 of the observation device 5. That is, observation of the sample in the container 7 mounted on the mounting table 4 is not disturbed by the mounting table 4.

<Container Tray>

As shown in FIG. 7 to FIG. 9, in the container tray 8, an elastic body 82 is arranged on the mounting surface 811 of the mounting plate 81 along an outer edge of the mounting region R, around the mounting region R of the container 7 and on the outer side of the mounting region R, and a slit 821 is formed in the elastic body 82. Accordingly, in this embodiment, the elastic body 82 has a C-shape extending along the outer edge of the mounting region R. The C-shaped elastic body 82 is merely an example, and the elastic body 82 may have various shapes according to the shape of the container 7.

A U-shaped first plate spring member 83 extending along an outer circumferential surface of the elastic body 82 is provided around the elastic body 82. The first plate spring member 83 crosses the slit 821 of the elastic body 82. Both ends 831, 832 of the first plate spring member 83 are bent outward. On the outside of the outer circumferential surface of the elastic body 82, the first plate spring member 83 may be arranged so as to have a gap between the first plate spring member 83 and the outer circumferential surface of the elastic body 82.

A pressing member 84 that presses and fixes the elastic body 82 onto the mounting surface 811 is further fixed to the mounting surface 811 of the mounting plate 81. Specifically, the pressing member 84 sandwiches a region of the elastic body 82 opposite to a region provided with the slit 821 between the pressing member 84 and the mounting surface 811. Thereby, the pressing member 44 presses the region of the elastic body 82 onto the mounting surface 811. Accordingly, the region of the elastic body 82 opposite to the region provided with the slit 821 is sandwiched between the pressing member 84 and the mounting plate 81.

A pair of screw members 841, 842 are screwed into the pressing member 84 through the ends 831, 832 of the first plate spring member 83, respectively. The first screw member 841 of the pair of screw members 841, 842, which passes through the bottom end 831 of the first plate spring member 83, is fastened by the pressing member 84. Therefore, the bottom end 831 of the first plate spring member 83 is fixed to the pressing member 84.

The second screw member 842 of the pair of screw members 841, 842, which passes through the front end 832 of the first plate spring member 83, is screwed into the pressing member 84 in a condition where its screwed amount can be adjusted. Accordingly, by adjusting the screwed amount of the second screw member 842, the first plate spring member 83 is elastically deformed using the bottom end 831 as a fixed point.

Figure 10:
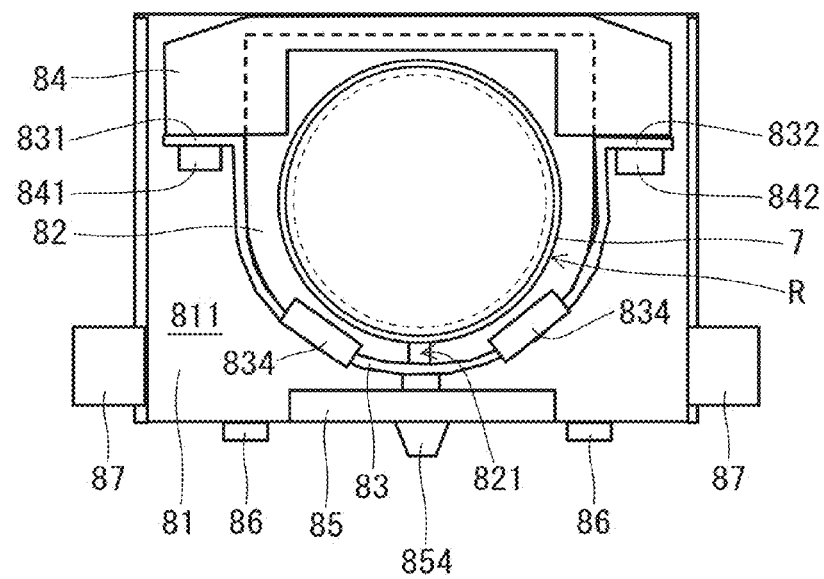
FIG. 10 is a top view for describing a biased state of a biasing mechanism of the container tray in the mounting table.
Figure 11:
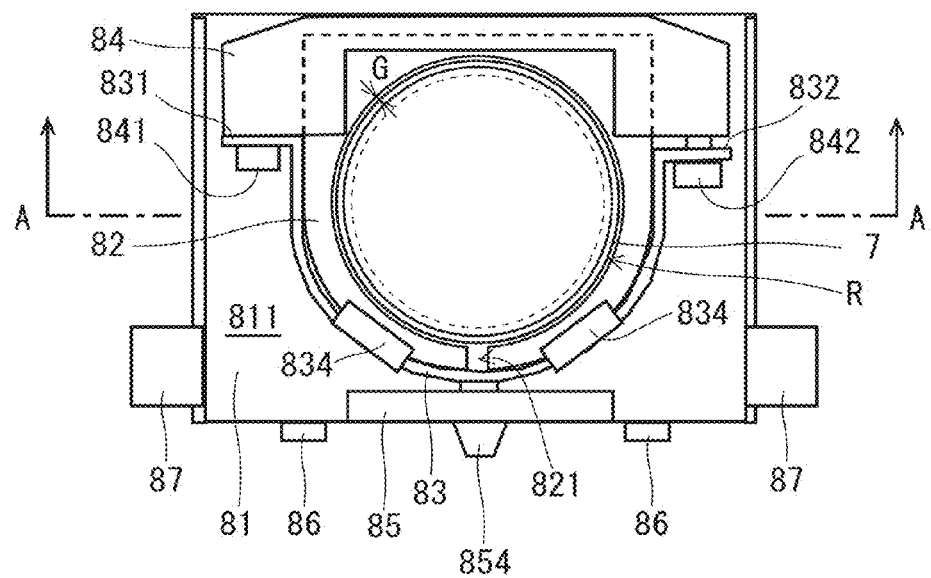
FIG. 11 is a top view for describing a bias released state of the biasing mechanism.

Specifically, as shown in FIG. 10, by screwing the second screw member 842 into the pressing member 84 to increase the screwed amount of the second screw member 842, the first plate spring member 83 is elastically deformed. At this time, a pressing force is applied to the elastic body 82 from the outside, and consequently, the elastic body 82 is biased inward. On the other hand, as shown in FIG. 11, by releasing the screwing of the second screw member 842 to reduce the screwed amount of the second screw member 842, elastic deformation of the first plate spring member 83 is alleviated or the first plate spring member 83 is released from elastic deformation. As a result, the bias on the elastic body 82 is released.

Thus, there is provided a biasing mechanism capable of changing states between a biased state (refer to FIG. 10) in which the elastic body 82 is biased inward by applying the pressing force to the elastic body 82 from the outside by means of the first plate spring member 83 and the second screw member 842 and a bias released state (refer to FIG. 11) in which the bias on the elastic body 82 is released.

The elastic body 82 has a small gap G between the elastic body 82 and the mounting region R of the container 7 while the biasing mechanism is set to the bias released state (refer to FIG. 11). For this reason, Where the container 7 is mounted on the mounting region R when the biasing mechanism is set to the bias released state, the side surface 72 of the container 7 is hardly brought into contact with the elastic body 82 (refer to FIG. 12B). Therefore, the elastic body 82 is prevented from being elastically deformed downward due to a frictional force generated between the side surface 72 of the container 7 and the elastic body 82. Thus, the container 7 does not receive the biasing force of causing the container 7 to float from the mounting surface 811 from the elastic body 82, and is mounted on the mounting surface 811 adhered closely to the mounting surface 811.

Since elastomer such as silicone rubber and chloroprene rubber is used as a material for the elastic body 82, the elastic body 82 has appropriate elasticity, frictional factor, and adherence.

The elastic body 82 has such a thickness that the elastic body 82 is not brought into contact with the cover 70 of the container 7 when the container 7 is mounted on the mounting region R of the mounting surface 811. Accordingly, when the container 7 is mounted on the mounting region R of the mounting surface 811, the elastic body 82 is not brought into contact with the cover 70 of the container 7, and thus, the cover 70 does not float from the container 7. Thus, any material contaminating the sample does not enter into the container 7.

As shown in FIG. 7 to FIG. 9, a rectangular-parallelepiped fixed body 85 is fixed to the mounting surface 811 of the mounting plate 81 in a region on the side of the slit 821 of the elastic body 82 along the outer edge of the mounting plate 81. The fixed body 85 has a recess 852 formed on a front surface 851 on the side of the elastic body 82, and a protrusion 854 provided in a central region of a front surface 853 opposite to the front surface 851.

The first plate spring member 83 has a projection 833 engaged with the recess 852 of the fixed body 85. The engagement between the projection 833 of the first plate spring member 83 and the recess 852 of the fixed body 85 prevents the first plate spring member 83 from floating from the mounting surface 811.

The first plate spring member 83 is further provided with a pair of left and right blocking members 834, 834 that prevent the elastic body 82 from moving with respect to the mounting surface 811 in a vertical direction (direction in which the plate spring member 83 floats from the mounting surface 811).

As shown in FIG. 7 to FIG. 9, the mounting plate 81 has a pair of left and right gripping parts 87, 87. Alternatively, a pair of left and right projections 86, 86 are formed on the outer circumferential surface of the mounting plate 81 in a region on the side of the slit 821 of the elastic body 82.

The configuration of the above-mentioned container tray 8 is simple. Therefore, disassembly and assembly of the container tray 8 are easy. Thus, before mounting the container 7 on the container tray 8, each component of the container tray 8 can be washed. An organic solvent is used for washing, and thus, it is preferred that each component of the container tray 8 is made of a material having a resistance to the organic solvent.

<Tray Base>

As shown in FIG. 7 to FIG. 9, the tray base 9 is detachably coupled to the lower side 261 of the X-axis sliding body 26 with two screw members 90, 90. The tray base 9 has an arrangement surface 91 on which the container tray 8 is arranged, and a pair of left and right second plate spring members 92, 92 are fixed to the arrangement surface 91 on both sides of a coupling region of the X-axis sliding body 26. Each of the second plate spring members 92 is arranged so as to have an elastic force in the Y-axis direction when being elastically deformed. Each of the second plate spring members 92 is positioned and is shaped such that the second plate spring member 92 is brought into contact with the pressing member 84 of the container tray 8 when the container tray 8 is arranged on the arrangement surface 91.

As shown in FIG. 7, the tray base 9 is provided with a bent part 94 at a front edge 93 in the Y-axis direction. The bent part 94 is formed by bending the tray base 9 substantially perpendicular to the arrangement surface 91. The bent part 94 has a fitted recess 941 formed in the central region thereof. When the container tray 8 is arranged on the arrangement surface 91, the protrusion 854 of the container tray 8 is fitted into the fitted recess 941. The bent part 94 further has a pair of left and right engagement receiving parts 942, 942 on both sides of a region provided with the fitted recess 941. When the container tray 8 is arranged on the arrangement surface 91, the pair of projections 86, 86 of the container tray 8 are engaged with the pair of engagement receiving parts 942, 942, respectively.

When the container tray 8 is arranged on the arrangement surface 91 of the tray base 9, the pair of second plate spring members 92, 92 of the tray base 9 are pressed by the pressing member 84 of the container tray 8 to deform the pair of the second plate spring member 92, 92. As a result, the container tray 8 is biased in the Y-axis direction by the elastic force of the pair of second plate spring members 92, 92.

Thus, the protrusion 854 of the container tray 8 is fitted into the fitted recess 941 of the tray base 9, and the projections 86 of the container tray 8 are engaged with the engagement receiving parts 942 of the tray base 9. The mounting plate 81 of the container tray 8 or the fixed body 85 is brought into contact with the bent part 94 of the tray base 9. Accordingly, the fitting of the protrusion 854 into the fitted recess 941 defines the position of the container tray 8 in the X-axis direction with respect to the tray base 9, the contact of the container tray 8 with the bent part 94 defines the position of the container tray 8 in the Y-axis direction with respect to the tray base 9, and the engagement between the engagement receiving parts 942 and the projections 86 defines the position of the container tray 8 in the Z-axis direction with respect to the tray base 9. As a result, the container tray 8 is detachably positioned at the predetermined position with respect to the tray base 9 (that is, the predetermined position on the arrangement surface 91 of the tray base 9).

In this manner, in the container tray 8 and the tray base 9, the protrusion 854 and the projections 86 of the container tray 8, and the pair of second plate spring members 92, 92, the fitted recess 941, and the pair of engagement receiving parts 942, 942 of the tray base 9 constitute the positioning mechanism for detachably fixing the container tray 8 to the tray base 9 at a predetermined position. In the tray base 9, the pair of second plate spring members 92, 92, the fitted recess 941, and the pair of engagement receiving parts 942, 942 of the tray base 9 constitute the positioning part for detachably fixing the container tray 8 to the arrangement surface 91 at a predetermined position.

<Method of Attaching Container to Container Tray>

Figure 12A:
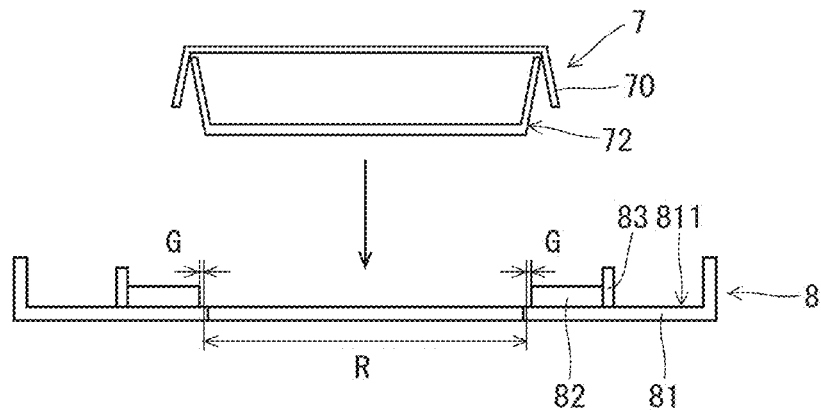
FIG. 12A is vertical sectional view for describing a first step of a method of attaching the container to the container tray.
Figure 12B:
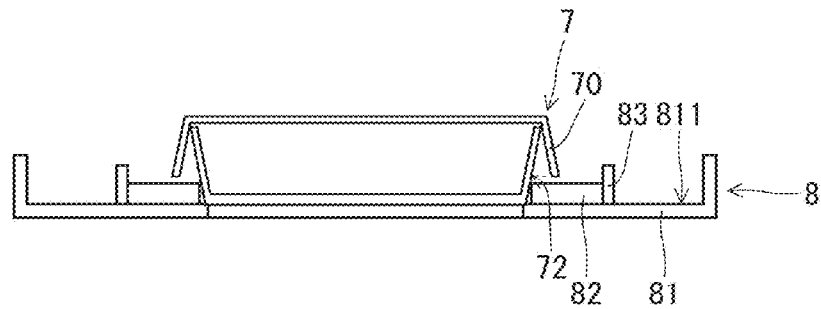
FIG. 12B is vertical sectional view for describing a first step of a method of attaching the container to the container tray.
Figure 13:
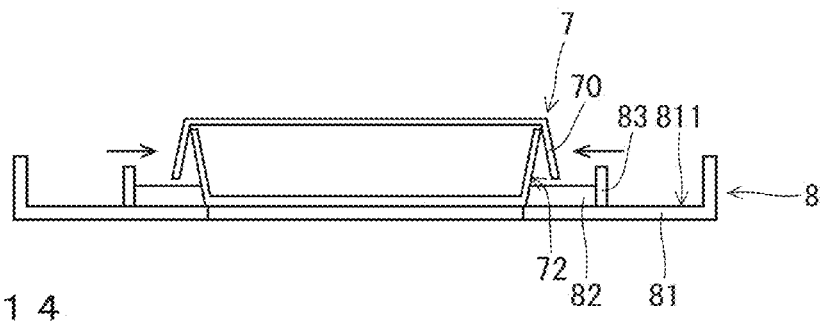
FIG. 13 is a vertical sectional view for describing a second step of the method of attaching the container to the container tray.

A method of attaching the container 7 to the container tray 8 will be specifically described with reference to the drawings. FIG. 12A and FIG. 12B are vertical sectional views for describing a first step of the method of attaching the container 7 to the container tray 8. FIG. 13 is a vertical sectional view for describing a second step of the method of attaching the container 7 to the container tray 8. These figures are sectional views taken along line A-A shown in FIG. 11. The first and second steps correspond to top views in FIG. 11 and FIG. 10, respectively.

First, in the first step, as shown in FIG. 11, by releasing the screwing of the second screw member 842 to reduce the screwed amount of the second screw member 842, the biasing mechanism is set to the bias released state. At this time, as shown in FIG. 12A, there is the small gap G between the elastic body 82 and the mounting region R of the container 7. For this reason, as shown in FIG. 12B, when the container 7 is mounted on the mounting region R, the side surface 72 of the container 7 is hardly brought into contact with the elastic body 82. Therefore, the elastic body 82 is prevented from being elastically deformed downward due to a frictional force generated between the side surface 72 of the container 7 and the elastic body 82. Thus, the container 7 does not receive the biasing force that causes the container 7 to float from the mounting surface 811 from the elastic body 82, and therefore, the container 7 is mounted and adhered closely to the mounting surface 811.

Next, in the second step, as shown in FIG. 10, by screwing the second screw member 842 into the pressing member 84 to increase the screwed amount of the second screw member 842, the biasing mechanism is set to the biased state. At this time, the pressing force is applied to the elastic body 82 from the outside due to elastic deformation of the first plate spring member 83, and the elastic body 82 is biased inward. Therefore, as shown in FIG. 13, the elastic body 82 is pressed onto the side surface 72 of the container 7, and adhered closely to the side surface 72. As a result, the container 7 is held by the elastic body 82. Accordingly, the container 7 is fixed to the mounting region R of the mounting surface 811 by the elastic body 82.

While the elastic body 82 is pressed onto the side surface 72 of the container 7 by the biasing mechanism, a wobble hardly occurs. The elastic body 82 has appropriate elasticity, appropriate frictional factor, and appropriate adherence. Therefore, even when the side surface 72 of the container 7 is inclined, a force to push up the container 7 hardly occurs. Accordingly, when the container 7 is held by the elastic body 82, the container 7 does not float from the mounting surface 811.

In the container tray 8, the container 7 is fixed to the mounting surface 811 of the mounting plate 81, and the container 7 is maintained in a condition where the container is adhered closely to the mounting surface 811. Accordingly, the position and orientation of the container 7 are hardly displaced from the predetermined position and orientation determined when the container 7 is fixed to the container tray 8.

Moreover, in the container tray 8, when the biasing mechanism is set to the biased state and the elastic body 82 is pressed onto the side surface 72 of the container 7, a force to cause the elastic body 82 to float from the mounting surface 811 may be generated in the elastic body 82. However, the first plate spring member 83 of the container tray 8 is provided with the pair of blocking members 834, 834. Therefore, the floating of the elastic body 82 is prevented by the pair of blocking members 834, 834. Accordingly, the container 7 is maintained in a condition where the container is adhered closely to the mounting surface 811.

Further, since the mounting plate 81 of the container tray 8 is provided with the pair of left and right gripping parts 87, 87, attachment and detachment of the container 7 to and from the container tray 8 is easy.

<Method of Attaching Container Tray to Tray Base>

Figure 14:
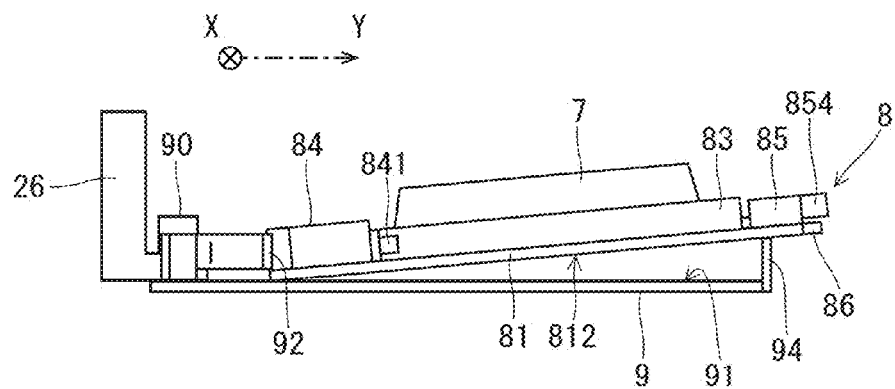
FIG. 14 is a side view for describing a first step of a method of attaching the container tray to the tray base.
Figure 15:
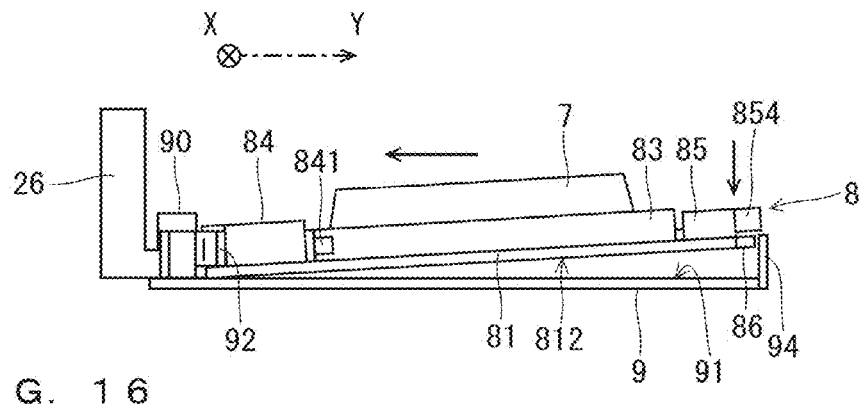
FIG. 15 is a side view for describing a second step of the method of attaching the container tray to the tray base.
Figure 16:
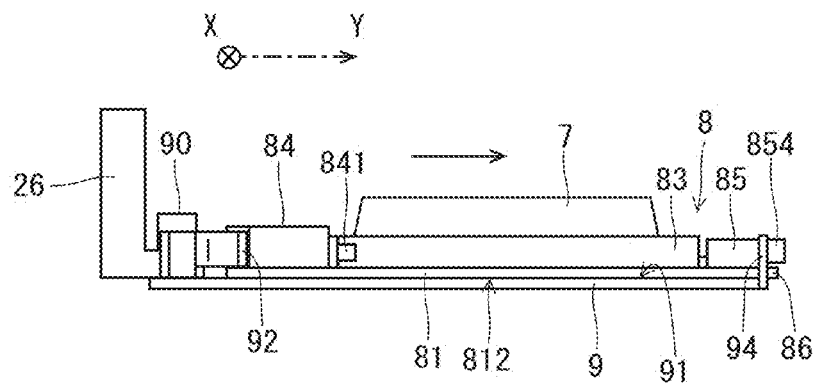
FIG. 16 is a side view for describing a third step of the method of attaching the container tray to the tray base.
Figure 17:
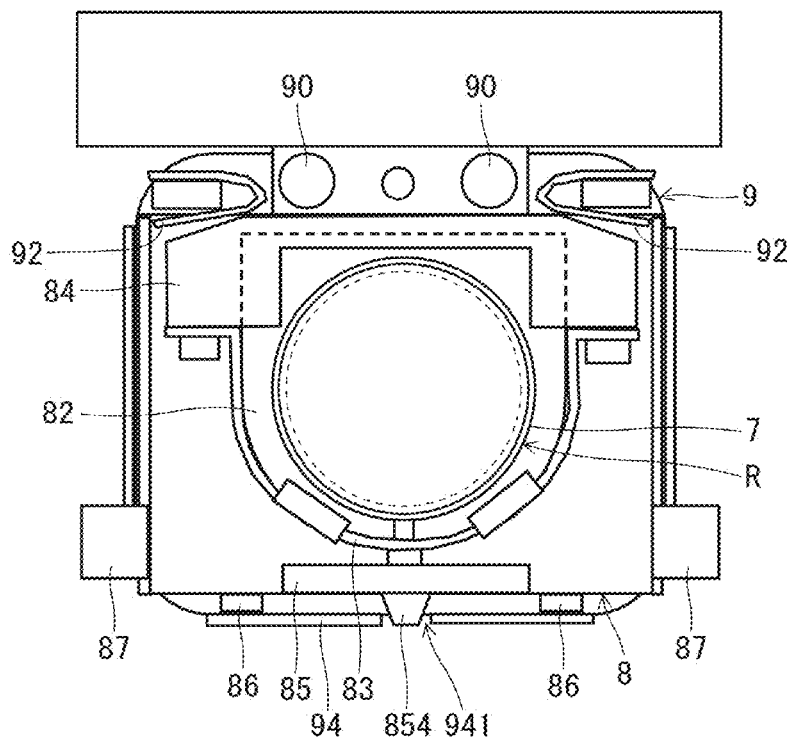
FIG. 17 is a top view for describing the second step of the method of attaching the container tray to the tray base.

Next, a method of attaching the container tray 8 to the tray base 9 will be specifically described with reference to the drawings. FIG. 14 to FIG. 16 are side views for describing a first step to a third step of the method of attaching the container tray 8 to the tray base 9, respectively. FIG. 17 is a top view which corresponds to the second step. FIG. 9 is also used to describe the first step.

First, in the first step, as shown in FIG. 9, the container tray 8 is moved closer to the tray base 9 in the Y-axis direction while orienting the pressing member 84 to the pair of second plate spring members 92, 92 of the tray base 9. Then, as shown in FIG. 14, by sliding the container tray 8 on the arrangement surface 91 of the tray base 9, the pressing member 84 of the container tray 8 is brought into contact with the pair of second plate spring members 92, 92 of the tray base 9. At this time, a front end of the bent part 94 of the tray base 9 is brought into contact with a back surface 812 of the mounting plate 81 of the container tray 8 and therefore, the container tray 8 is inclined.

In the second step, as shown in FIG. 15 and FIG. 17, by pressing the container tray 8 in a direction opposite to the Y-axis direction against the elastic force of the pair of second plate spring members 92, 92 of the tray base 9, the container tray 8 is further slid on the arrangement surface 91 of the tray base 9. Accordingly, the second plate spring members 92, 92 are elastically deformed.

At this time, the container tray 8 is slid in the direction opposite to the Y-axis direction until front ends of the pair of projections 86, 86 reach the inner side of the bent part 94 of the tray base 9. Accordingly, the container tray 8 can be pushed downward to adhere the back surface 812 of the mounting plate 81 of the container tray 8 closely to the arrangement surface 91 of the tray base 9.

In the third step, as shown in FIG. 16, after the back surface 812 of the mounting plate 81 of the container tray 8 is adhered closely to the arrangement surface 91 of the tray base 9, the container tray 8 is slid in the Y-axis direction while adhered closely to the arrangement surface 91 by using the elastic force of the pair of second plate spring members 92, 92 of the tray base 9. Accordingly, as shown in FIG. 7, the protrusion 854 of the container tray 8 is fitted into the fitted recess 941 of the tray base 9, and the engagement receiving parts 942 of the tray base 9 are engaged with the respective projections 86 of the container tray 8. The mounting plate 81 of the container tray 8 or the fixed body 85 is adhered closely to the bent part 94 of the tray base 9. As a result, the container tray 8 is detachably positioned on the tray base 9 at the predetermined position.

When the container tray 8 is detached from the tray base 9, the first step to the third step may be executed in the reverse order.

In the mounting table 4, when the exchange operation of the culture medium in the container 7 mounted on the mounting table 4 is performed, the container tray 8 can be detached from the tray base 9 in a condition where the container 7 is fixed to the container tray 8. Then, after the completion of the exchange operation, the container tray 8 can be reattached to the tray base 9. Even if the container tray 8 is detached from the tray base 9 as described above, when the container tray 8 is reattached to the tray base 9, the container tray 8 is positioned at the predetermined position on the tray base 9 as described above. The container 7 remains fixed to the container tray 8, and its position and orientation are not displaced from the predetermined position and orientation.

Thus, as described later (refer to steps S11, S12 in FIG. 19), even if the time lapse operation is temporarily stopped during the execution of the time lapse operation to perform the exchange operation of the culture medium, the position and orientation of the container 7 are hardly displaced before and after the execution of the exchange operation of the culture medium. Specifically, even if the position and orientation of the container 7 are displaced, a displaced amount is only a few μm, which hardly affects observation of the sample having a few hundreds of μm. That is, before and after the exchange operation, the coordinates and the focus position of the sample are hardly displaced from the coordinates and the focus position that are recorded in the memory as the sample information. Therefore, there is no need to set again the sample information necessary for the execution of the time lapse operation.

Further, in the mounting table 4, the mounting plate 81 of the container tray 8 are provided with the pair of left and right gripping parts 87, 87. Accordingly, attachment and detachment of the container tray 8 to and from the tray base 9 is easy.

Figure 18A:
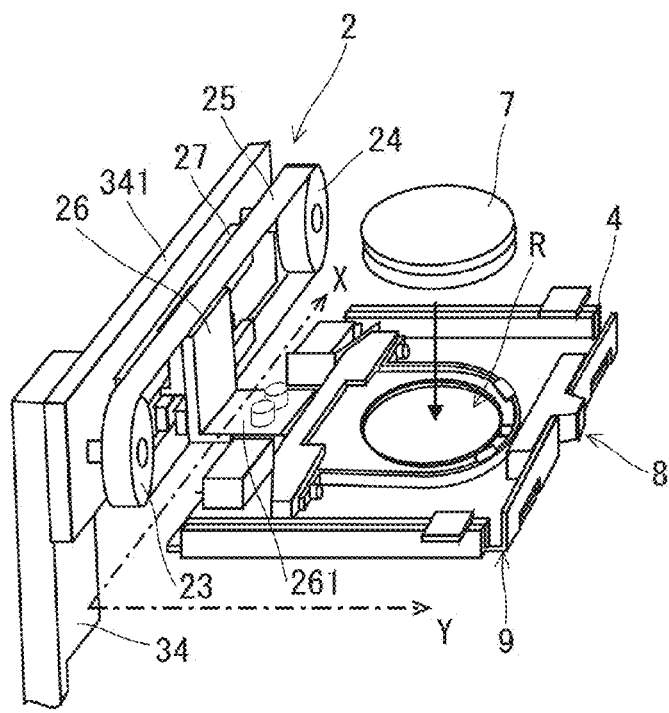
FIG. 18A is perspective view used for describing that the mounting table can be exchanged according to the size of the container.
Figure 18B:
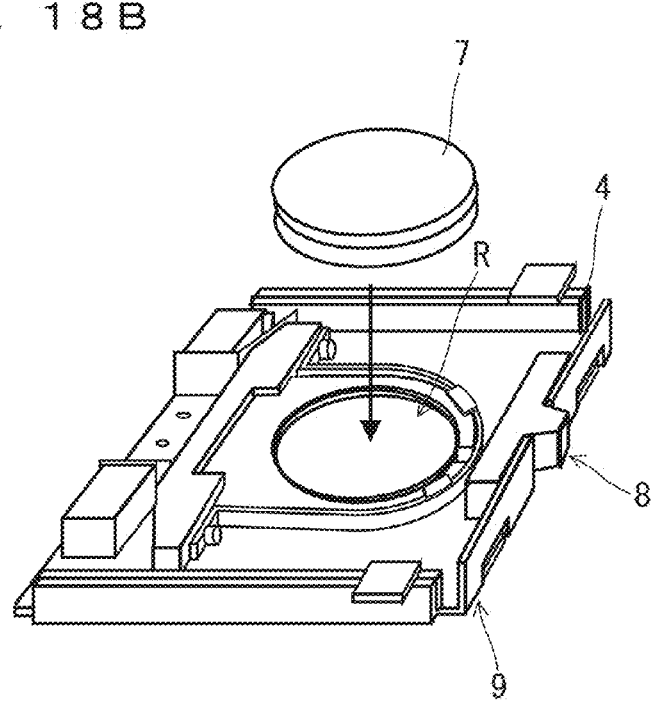
FIG. 18B is perspective view used for describing that the mounting table can be exchanged according to the size of the container.

FIG. 18A and FIG. 18B are perspective views used for describing that the mounting table 4 can be exchanged according to the size of the container 7. As shown in FIG. 18A and FIG. 18B, the plurality of mounting table 4 having different areas of the mounting region R of the container 7 may be prepared. In this case, the mounting table 4 can be exchanged according to the size of the used container 7.

2-6. Search Mode and Time Lapse Mode

The observation unit 100 has two modes of observing the sample using the observation unit 100, and observation unit 100 can be selectively set to either of the two modes.

One of the two modes is a search mode in which the user searches and determines one or more samples and records the sample information that varies according to the determined sample in the memory of the personal computer 103. The sample information includes coordinates, the zoom magnification factor, and the focus position of the sample. Hereinafter, an observing operation performed by the observation unit 100 in the search mode is referred to as "search operation".

The other of the two modes is an observing mode in which one or more samples is repeatedly observed by the observation device 5 on a certain cycle based on the sample information recorded in the memory of the personal computer 103 to acquire the observed image of the sample at each observation. Hereinafter, this observing mode is referred to as "time lapse mode", and the observing operation performed by the observation unit 100 in the time lapse mode is referred to as "time lapse operation". The time lapse operation is performed based on setting information previously set by the user in addition to the sample information. The setting information includes an observation point list on the execution of the time lapse operation, a start time, an end time, a time lapse cycle, and a storage place of the observed image.

3. Relay Control Part

The relay control part 102 controls the operation of the observation unit 100 based on a control signal outputted from the personal computer 103. Specifically, the relay control part 102 controls a light-emitting operation of an LED 61 of the observation unit 100, a relay operation of independently switching conduction and non-conduction of the observation unit 100 and its components, and a rotating operation of each motor of the observation unit 100.

4. Personal Computer 4-1. Configuration of Personal Computer

The personal computer 103 includes a controller that controls the observation unit 100 and the memory. The memory records therein the sample information necessary for controlling the time lapse operation of the observation unit 100, and the observed image of the sample acquired by the CCD camera 54 of the observation unit 100. The control signal for controlling the observation unit 100 is outputted from the controller of the personal computer, and is inputted to the relay control part 102 via the cable 106.

When the user selects the search mode as the mode set to the observation unit 100 in the personal computer 103, the controller of the personal computer 103 shifts to a state where the controller can control the search operation of the observation unit 100. In this manner, the observation unit 100 is set to the search mode. At this time, based on an operation command inputted into the personal computer 103 by the user, the controller controls the search operation of the observation unit 100 via the relay control part 102. Accordingly, the rotating operation of each motor of the observation unit 100 is controlled according to the operation command inputted by the user, whereby the coordinates, the zoom magnification factor, and the focus position of the sample arranged at the observation point M are changed.

When the user inputs a determination command in the personal computer 103 to determine the sample to be observed, the controller of the personal computer 103 receives the determination command and records the sample information on the sample arranged at the observation point M at this time in a memory 70.

On the other hand, when the user selects the time lapse mode as the mode set to the observation unit 100 in the personal computer 103, the controller of the personal computer 103 shifts to the state where the controller can control the time lapse operation of the observation unit 100. In this manner, the observation unit 100 is set to the time lapse mode. At this time, the controller reads the sample information and the setting information recorded in the memory, and controls the time lapse operation of the observation unit 100 based on the sample information and the setting information. Accordingly, the rotating operation of each motor of the observation unit 100 and the imaging operation of the CCD camera 54 of the observation unit 100 are controlled according to the sample information and the setting information. As a result, the observed images of all samples that are to be acquired by the user are acquired.

4-2. Flow of Observing Operation Procedure

Figure 19:
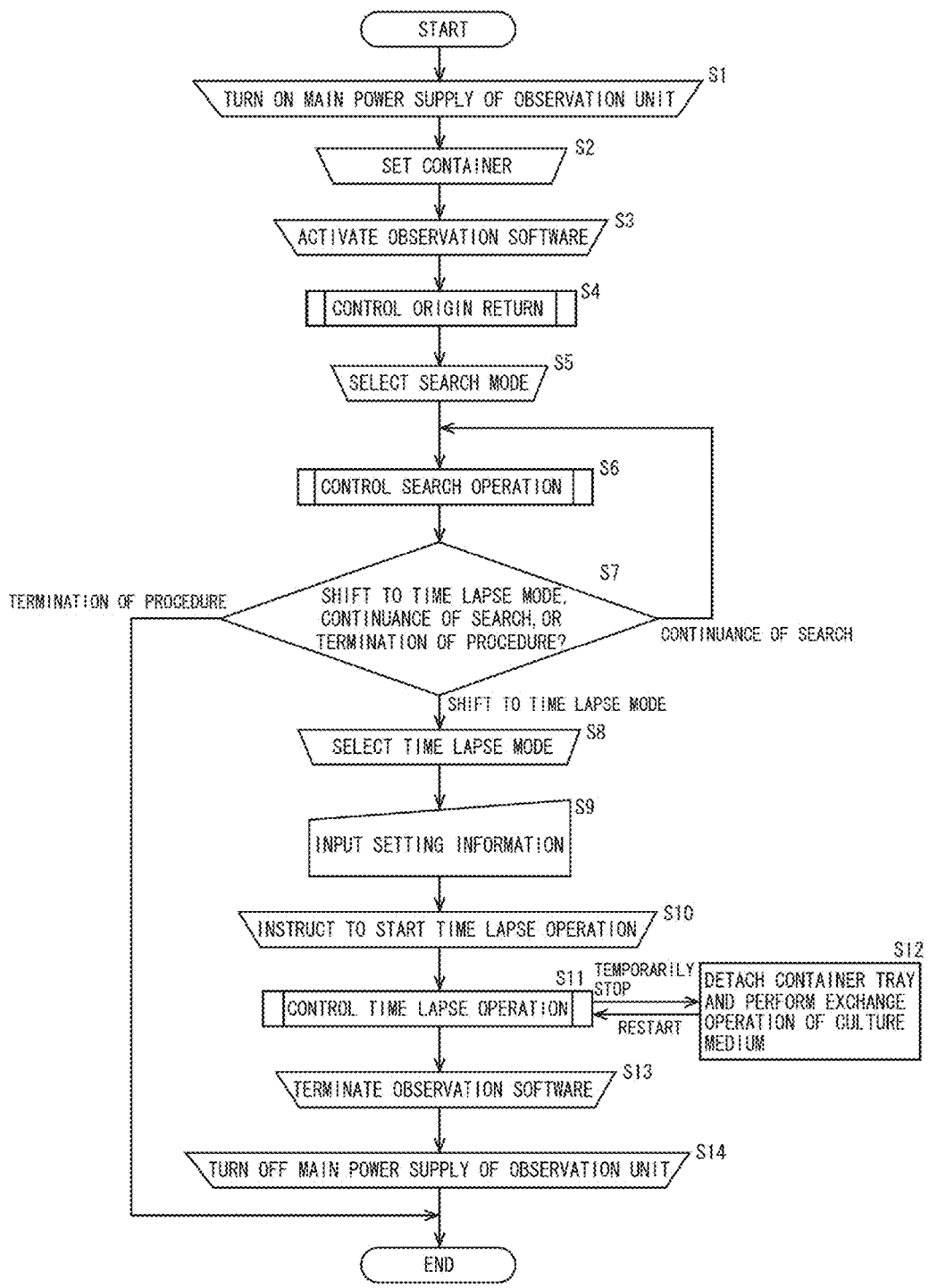
FIG. 19 is a flowchart showing an observing operation procedure executed in the observation system.

FIG. 19 is a flowchart showing an observing operation procedure executed in the observation system. When the observing operation procedure is started in the observation system, first, in step S1, the user operates a power switch (not shown) provided in the relay control part 102 to turn on a main power supply of the observation unit 100.

Then, in step S2, the user mounts the container 7 on the mounting table 4. Specifically, the container 7 is fixed to the mounting table 4 by using "the method of attaching the container to the container tray" and "the method of attaching the container tray to the tray base" described above.

Next, in step S3, the user activates observation software on the personal computer 103. Thereafter, in step S4, the controller of the personal computer 103 executes origin return control. Specifically, the controller returns the mounting table 4 to the origin in the XY coordinate system by using the X-axis origin sensor 28 and the Y-axis origin sensor 36. The controller returns the observation device 5 to the origin in the Z-axis direction using the Z-axis origin sensor 57, and returns the zoom lens 53 to the predetermined position using the zoom original sensor 55.

Next, in step S5, the user selects the search mode as the mode set to the observation unit 100. Accordingly, the controller of the personal computer 103 shifts to the state where the controller can control the search operation of the observation unit 100, and the observation unit 100 is set to the search mode.

Then, in step S6, the controller of the personal computer 103 controls the search operation. Specifically, the user searches and determines one or more samples by using the observation device 5. The controller records the sample information (coordinates, the zoom magnification factor, and focus position of the sample) that varies according to each of the determined samples in the memory of the personal computer 103.

After execution of step S6, in step S7, the user selects any of the options: shift to the time lapse mode; continuance of the search for the sample; and termination of the observing operation procedure. If the continuance of the search for the sample is selected in step S7, the observing operation procedure returns to step S6, and the controller of the personal computer 103 controls the search operation again. Then, in step S7, step S6 is repeated until an option other than the continuance of the search for the sample is selected, and the sample information on a plurality of sample to be observed is recorded in the memory. On the other hand, if the termination of the observing operation procedure is selected in step S7, the observing operation procedure is finished.

In contrast, if the shift to the time lapse mode is selected in step S7, the user selects the time lapse mode as the mode set to the observation unit 100 in step S8. Accordingly, the controller of the personal computer 103 shifts to the state where the controller can control the time lapse operation of the observation unit 100, and the observation unit 100 is set to the time lapse mode.

Thereafter, in step S9, the user operates to input the setting information (the observation point list, the start time, the end time, the time lapse cycle, and the storage place of the observed image) necessary for performing the time lapse operation in the observation unit 100. Then, when the user inputs a start command to start the execution of the time lapse operation to the controller of the personal computer 103 in step S10, the controller controls the time lapse operation in step S11.

Specifically, in step S11, one or more samples is repeatedly observed by the observation device 5 on a certain cycle based on the sample information and the setting information recorded in the memory of the personal computer 103, and the observed image of the sample is acquired at each observation. Then, the acquired observed image is recorded in the memory of the personal computer 103.

After control of the time lapse operation is temporarily stopped in step S11, the container tray 8 can be detached from the tray base 9 in step S12 to perform the exchange operation of the culture medium. After execution of step S12, the container tray 8 can be reattached to the tray base 9 to restart the control of the time lapse operation.

After execution of step S11, in step S13, the user terminates the observation software on the personal computer 103. Then, in step S14, the user operates the power switch (not shown) provided in the relay control part 102 to turn off the main power supply of the observation unit 100. This terminates the observing operation procedure in the observation system.

5. Modifications

The configuration of each component of the present invention is not limited to the embodiment, and may be variously modified within the technical scope described in the claims. Three modifications will be specifically described below.

5-1. First Modification

Figure 20:
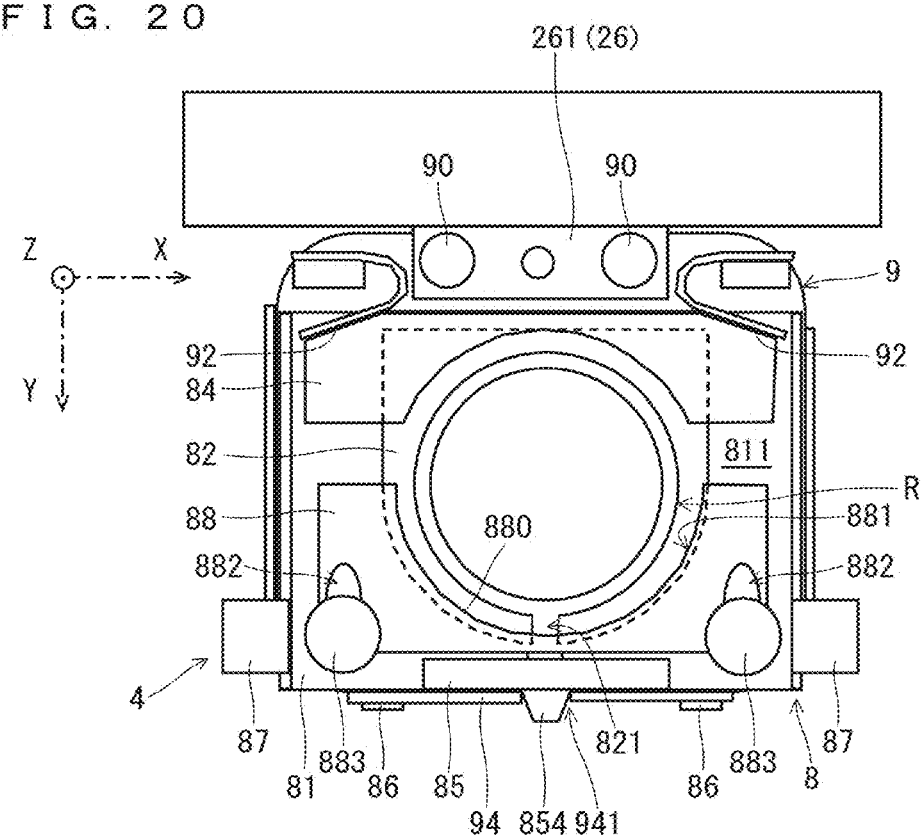
FIG. 20 is a top view showing a first modification of the mounting table.

FIG. 20 is a top view showing a first modification of the mounting table 4. As shown in FIG. 20, the container tray 8 may be provided with a movable body 88 that can slide in the Y-axis direction, in place of the first plate spring member 83. The movable body 88 has a recess 881, and an inner surface of the recess 881 is curved in a U-shaped along the outer circumferential surface of the elastic body 82. The inner surface of the recess 881 of the movable body 88 extends across the slit 821 of the elastic body 82.

The inner surface of the recess 881 has a U-shaped flange 880 that covers a part of the outer edge of the elastic body 82. In this modification, the flange 880 functions as a blocking member that blocks the elastic body 82 from moving in the direction perpendicular to the mounting surface 811 (the direction in which the elastic body 82 floats from the mounting surface 811).

The movable body 88 is provided with a pair of left and right vertical long through holes 882, 882 extending in the Y-axis direction, and a pair of screw members 883, 883 are inserted into the pair of through holes 882, 882, respectively. Each of the screw members 883 is screwed into the mounting plate 81 of the container tray 8 in a state where the screwed amount can be adjusted.

Accordingly, by releasing the pair of screw members 883, 883 to reduce the screwed amount of each of the screw members 883, the movable body 88 can be slid. On the other hand, by screwing the pair of screw members 883, 883 to increase the screwed amount of each of the screw members 883, the movable body 88 is fixed to the mounting surface 811 of the mounting plate 81. Thus, the movable body 88 can be fixed at various positions in its movable range.

In the movable body 88, by sliding the movable body 88 in the direction opposite to the Y-axis direction and pressing the inner surface of the recess 881 onto the elastic body 82 and then, fixing the movable body 88 to the mounting surface 811, the pressing force is applied to the elastic body 82 from the outside. As a result, the elastic body 82 is biased inward (biased state). In contrast, by sliding the movable body 88 in the Y-axis direction, the bias on the elastic body 82 is released (bias-released state).

Accordingly, in the first modification, the movable body 88 constitutes a biasing mechanism capable of changing states between the biased state and the bias-released state.

In the mounting table 4 in the first modification, similarly to the mounting table 4 shown in FIG. 7 and FIG. 8, the position and orientation of the container 7 are hardly displaced from the predetermined position and orientation determined when the container 7 is fixed to the container tray 8.

5-2. Second Modification

Figure 21:
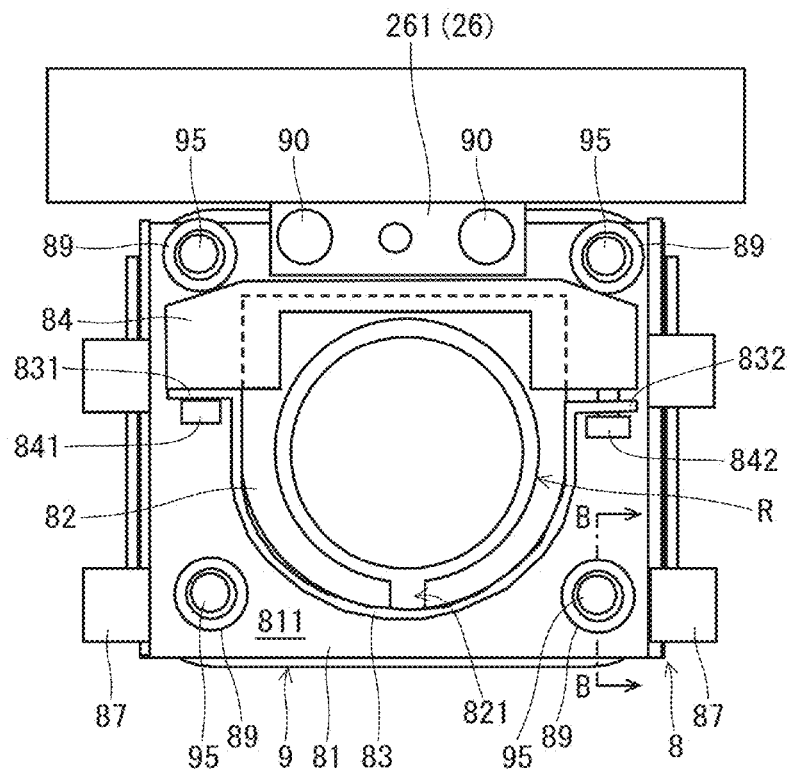
FIG. 21 is a top view showing a second modification of the mounting table.
Figure 22:
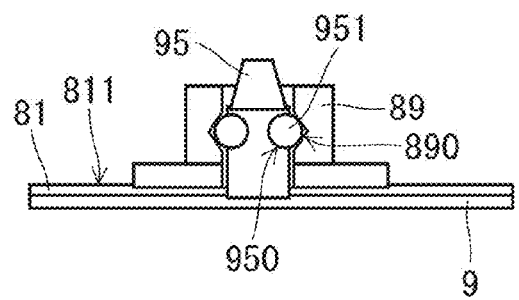
FIG. 22 is a sectional view taken along line B-B shown in FIG. 21.

FIG. 21 is a top view showing a second modification of the mounting table 4. FIG. 22 is a sectional view taken along line B-B shown in FIG. 21. The container tray 8 and the tray base 9 may be provided with another positioning mechanism in place of the positioning mechanism of the mounting table 4 in FIG. 7 and FIG. 8. Specifically, as shown in FIG. 21, pin members 95 protrude from four places on the arrangement surface 91 of the tray base 9, and pin receiving parts 89 are formed in the mounting plate 81 of the container tray 8. The respective pin members 95 are inserted into the pin receiving parts 89 from the side of the back surface 812.

As shown in FIG. 22, an annular groove 950 is formed in an outer circumferential surface of each of the pin members 95, and an elastic ring body 951 is fitted into the groove 950. An engaging groove 890 engaged with the ring body 951 of the pin member 95 inserted into each of the pin receiving parts 89 is depressingly formed on an inner circumferential surface of each of the pin receiving parts 89. The engaging groove 890 is formed so as to engage with the ring body 951 when the back surface 812 of the mounting plate 81 is adhered closely to the arrangement surface 91 of the tray base 9.

In the mounting table 4 according to the second modification, the position of the container tray 8 in the X-axis direction and the Y-axis direction with respect to the tray base 9 is defined by inserting the pin members 95 into the respective pin receiving parts 89. The position of the container tray 8 in the Z-axis direction with respect to the tray base 9 is defined by engaging the ring body 951 with the engaging groove 890. As a result, by merely inserting the pin members 95 into the pin receiving parts 89, the container tray 8 can be detachably positioned at the predetermined position with respect to the tray base 9.

5-3. Third Modification

Figure 23:
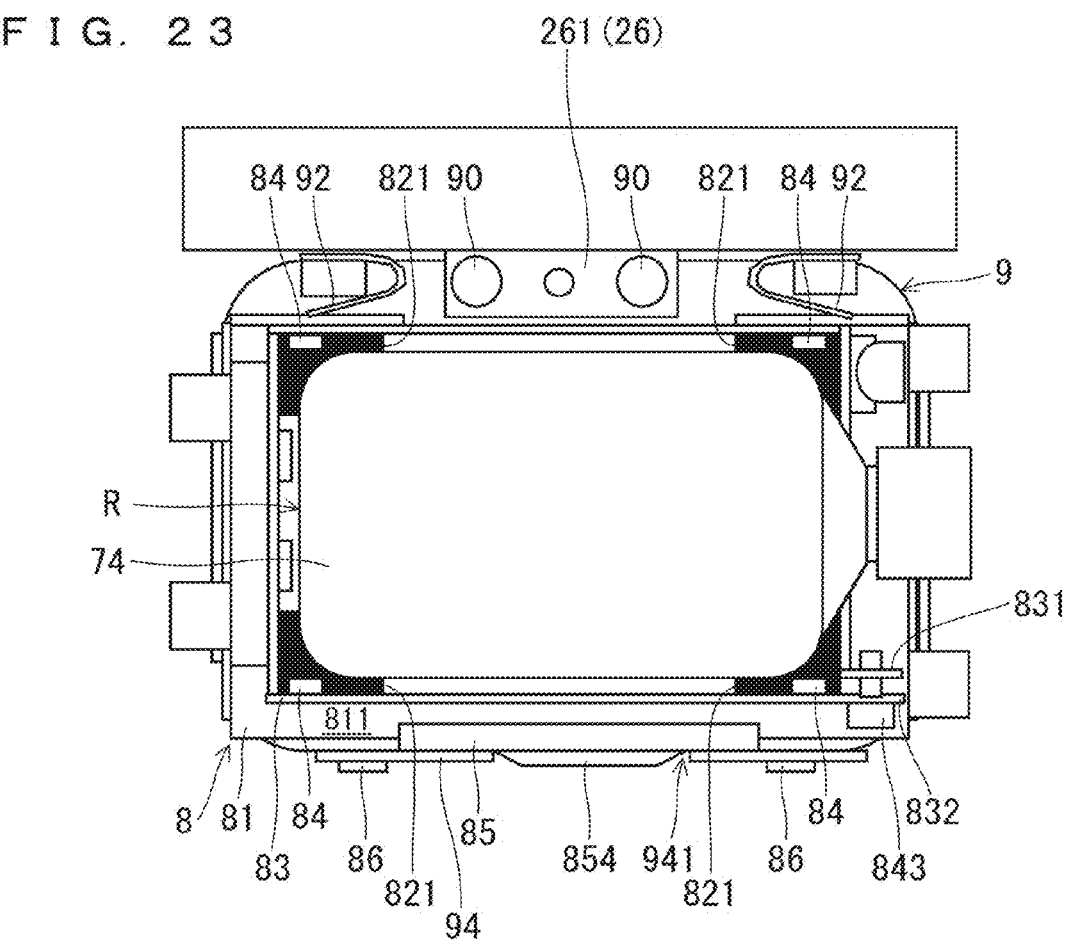
FIG. 23 is a top view showing a third modification of the mounting table.

FIG. 23 is a top view showing a third modification of the mounting table 4. As shown in FIG. 23, the mounting table 4 may have a configuration applicable to a square container 74, for example, a flask-shaped container having a cap. Specifically, the elastic body 82 is formed of four elastic body pieces 821 to 821, and the four elastic body pieces 821 to 821 are arranged so as to correspond to four corners of the square container 74 around the mounting region R of the square container 74.

The first plate spring member 83 surrounds the four elastic body pieces 821 to 821 in the shape of a substantially rectangular frame. One end 831 of the first plate spring member 83 is bent outward so as to oppose to the other end 832. One screw member 843 is screwed into the one end 831 through the other end 832. The screw member 843 is screwed into the one end 831 such that the screwed amount can be adjusted. Accordingly, by adjusting the screwed amount of the screw member 843, the first plate spring member 83 is elastically deformed.

The first plate spring member 83 according to this modification is provided with the blocking members 834 that prevent the elastic body pieces 821 from moving in a direction perpendicular to the mounting surface 811 (direction in which the elastic body pieces 821 float from the mounting surface 811) at four places.

In the mounting table 4 according to the third modification, by screwing the screw member 843 into the one end 831 to increase the screwed amount of the screw member 843, the first plate spring member 83 is elastically deformed. At this time, the pressing force is applied to the four elastic body pieces 821 to 821 from the outside, and consequently, the four elastic body pieces 821 to 821 are biased inward (biased state). In contrast, by releasing the screwing of the screw member 843 to reduce the screwed amount of the screw member 843, elastic deformation of the first plate spring member 83 is alleviated, or the first plate spring member 83 is released from elastic deformation. As a result, the bias on the four elastic body pieces 821 to 821 is released (released state).

In the mounting table 4 according to the third modification, similarly to the mounting table 4 shown in FIG. 7 and FIG. 8, the position and orientation of the square container 74 are hardly displaced from the predetermined position and orientation determined when the square container 74 is fixed to the container tray 8.

The configuration of each component of the present invention is not limited to the embodiment, and may be variously modified within the technical scope defined in the claims. For example, the configuration of the biasing mechanism capable of changing states between the biased state and the bias released state is not limited to the above-mentioned configuration, and can be variously modified. The shape and position of the blocking members 834 are not limited to the above-mentioned configuration, and can be variously modified. Further, the elastic body 82 may extend along the outer edge of the mounting region R of the container in a C-shape as shown in FIG. 8, or may be formed of the plurality of elastic body pieces arranged around the mounting region R of the container as shown in FIG. 23.

The container tray 8 may be configured to fix the plurality of containers 7. Attachment of the container tray 8 to the tray base 9 may be automated.

The various configurations adopted for the observation unit 100 is not limited to the observation system used inside the storage 101, and can be applied to the observation unit used outside the storage 101. The various configurations adopted for the observation unit 100 can also be applied to an observation unit without the X-axis driving part 2 and/or the Y-axis driving part 3.

DESCRIPTION OF REFERENCE CHARACTERS 100 observation unit
1 housing
2 X-axis driving part
3 Y-axis driving part
4 mounting table
5 observation device
6 illuminating device
7 container
70 cover
72 side surface
8 container tray
81 mounting plate
811 mounting surface
812 back surface
82 elastic body 821 elastic body piece
83 first plate spring member
833 projection
834 blocking member
84 pressing member
841 first screw member
842 second screw member
843 screw member
85 fixed body
852 recess
854 protrusion
86 projection
87 gripping part
88 movable body
880 flange
881 recess
882 through hole
883 screw member
89 pin receiving part
890 engaging groove
9 tray base
90 screw member
91 arrangement surface
92 second plate spring member
94 bent part
941 fitted recess
942 engagement receiving part
95 pin member
950 groove
951 ring body

The invention claimed is:

1. A container tray comprising:
a mounting plate configured to include a mounting surface on which a container is to be mounted;
an elastic body arranged on the mounting surface of the mounting plate around a mounting region where the container is to be mounted; and
a biasing mechanism arranged around the elastic body, the biasing mechanism being capable of switching states between a biased state in which the elastic body is biased inward by applying a pressing force to the elastic body from outside and a bias released state in which the bias on the elastic body is released, wherein
when the biasing mechanism is set to the bias released state, there is a small gap between the elastic body and the mounting region of the container.

2. The container tray according to claim 1, wherein the biasing mechanism is provided with a blocking member that blocks the elastic body from moving in a direction perpendicular to the mounting surface.

3. The container tray according to claim 2, wherein the elastic body extends along an outer edge of the mounting region of the container in a C-shape, or is formed of a plurality of elastic body pieces arranged around the mounting region of the container.

4. A tray base comprising:
an arrangement surface on which the container tray according to claim 3 is arranged; and
a positioning part that detachably fixes the container tray at a predetermined position on the arrangement surface.

5. An observation unit comprising:
a mounting table on which a container is to be mounted;
a driving mechanism that drives the mounting table; and
an observation device that observes a sample in the container mounted on the mounting table, wherein
the mounting table is formed of the container tray according to claim 3, and a tray base on which the container tray is arranged, and
the container tray and the tray base are each provided with a positioning mechanism that detachably fixes the container tray to the tray base at a predetermined position.

6. A tray base comprising:
an arrangement surface on which the container tray according to claim 2 is arranged; and
a positioning part that detachably fixes the container tray at a predetermined position on the arrangement surface.

7. An observation unit comprising:
a mounting table on which a container is to be mounted;
a driving mechanism that drives the mounting table; and
an observation device that observes a sample in the container mounted on the mounting table, wherein
the mounting table is formed of the container tray according to claim 2, and a tray base on which the container tray is arranged, and
the container tray and the tray base are each provided with a positioning mechanism that detachably fixes the container tray to the tray base at a predetermined position.

8. The container tray according to claim 1, wherein the elastic body extends along an outer edge of the mounting region of the container in a C-shape, or is formed of a plurality of elastic body pieces arranged around the mounting region of the container.

9. A tray base comprising:
an arrangement surface on which the container tray according to claim 8 is arranged; and
a positioning part that detachably fixes the container tray at a predetermined position on the arrangement surface.

10. An observation unit comprising:
a mounting table on which a container is to be mounted;
a driving mechanism that drives the mounting table; and
an observation device that observes a sample in the container mounted on the mounting table, wherein
the mounting table is formed of the container tray according to claim 8, and a tray base on which the container tray is arranged, and
the container tray and the tray base are each provided with a positioning mechanism that detachably fixes the container tray to the tray base at a predetermined position.

11. A tray base comprising:
an arrangement surface on which the container tray according to claim 1 is arranged; and
a positioning part that detachably fixes the container tray at a predetermined position on the arrangement surface.

12. An observation unit comprising:
a mounting table on which a container is to be mounted;
a driving mechanism that drives the mounting table; and
an observation device that observes a sample in the container mounted on the mounting table, wherein
the mounting table is formed of the container tray according to claim 1, and a tray base on which the container tray is arranged, and
the container tray and the tray base are each provided with a positioning mechanism that detachably fixes the container tray to the tray base at a predetermined position.

* * * * *